United States Patent
Kandori et al.

(10) Patent No.: US 7,892,189 B2
(45) Date of Patent: Feb. 22, 2011

(54) MOVEMENT ANALYSIS DISPLAY APPARATUS AND MOVEMENT ANALYZING METHOD

(75) Inventors: Akihiko Kandori, Tokyo (JP); Tsuyoshi Miyashita, Fuchu (JP); Kuniomi Ogata, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 1116 days.

(21) Appl. No.: 11/350,722

(22) Filed: Feb. 10, 2006

(65) Prior Publication Data

US 2006/0244744 A1 Nov. 2, 2006

(30) Foreign Application Priority Data

Apr. 19, 2005 (JP) ............................. 2005-120584

(51) Int. Cl.
- *A61B 5/103* (2006.01)
- *A61B 5/117* (2006.01)
- *A61B 5/22* (2006.01)
- *A61B 1/24* (2006.01)
- *A63B 21/00* (2006.01)
- *A63B 23/16* (2006.01)
- *G01L 3/24* (2006.01)
- *G01L 5/00* (2006.01)

(52) U.S. Cl. .................... 600/595; 600/587; 73/379.01; 73/379.02

(58) Field of Classification Search ................. 600/595, 600/587, 372, 382, 384; 73/379.01, 379.02

See application file for complete search history.

(56) References Cited

U.S. PATENT DOCUMENTS

| 6,416,485 | B1 | 7/2002 | Rovetta et al. |
| 2002/0107649 | A1 | 8/2002 | Takiguchi et al. |
| 2005/0065422 | A1 | 3/2005 | Kandori et al. |

FOREIGN PATENT DOCUMENTS

| JP | 05-005784 | 1/1993 |
| JP | 2003-015810 | 1/2003 |
| WO | WO 01/06473 | 1/2001 |

OTHER PUBLICATIONS

Kandori et al., Quantitative magnetic detection of finger movements in patients with Parkinson's disease, Neuoriscience Research, col. 49, Issue 2, Jun. 2004 (available online May 6, 2004), pp. 253-260.*

(Continued)

*Primary Examiner*—Jeffrey G. Hoekstra
(74) *Attorney, Agent, or Firm*—Antonelli, Terry, Stout & Kraus, LLP.

(57) ABSTRACT

A movement analysis display apparatus includes a analyzing unit for analyzing waveform data of a time series which is acquired from a movement sensor, and a display unit for displaying an analysis result that is analyzed by the analyzing unit. The analyzing unit includes a movement waveform generating section for generating a movement waveform from the waveform data, an energy balance value calculating means for calculating a movement energy ratio in opposed movement directions in a velocity waveform, an envelope curve generating section for generating an envelope curve at a given time width in a distance waveform, and a time integration curve analyzing section for integrating a movement waveform with respect to time.

3 Claims, 18 Drawing Sheets

OTHER PUBLICATIONS

Quantitative Digitography (QDG): A Sensitive Measure Of Digital Motor Control in Idiopathic Parkinson's Disease; Helen M. Gronte-Stewart, MSE, MD, et al.; 2000; pp. 36-47, vol. 15, No. 1; Movement Disorders Society; United States.

Control of Repetitive Lip and Finger Movements in Parkinson's Disease: Influence of External Timing Signals and Simultaneous Execution on Motor Performance; J. Konczak, et al.; 1997; pp. 665-676, vol. 12, No. 5; Movement Disorder Society; United States.

Quantitative Magnetic Detection of Finger Movements in Patients with Parkinson's Disease; Akihiko Kandori, et al.; 2004; pp. 253-260; Neuroscience Research.

Quantitative Magnetic Detection Of Finger Movements In Patients With Parkinson's Disease, Kandori et al, XP-002468424, Neuroscience Research 49, 2004, 253-260.

* cited by examiner

FIG. 2
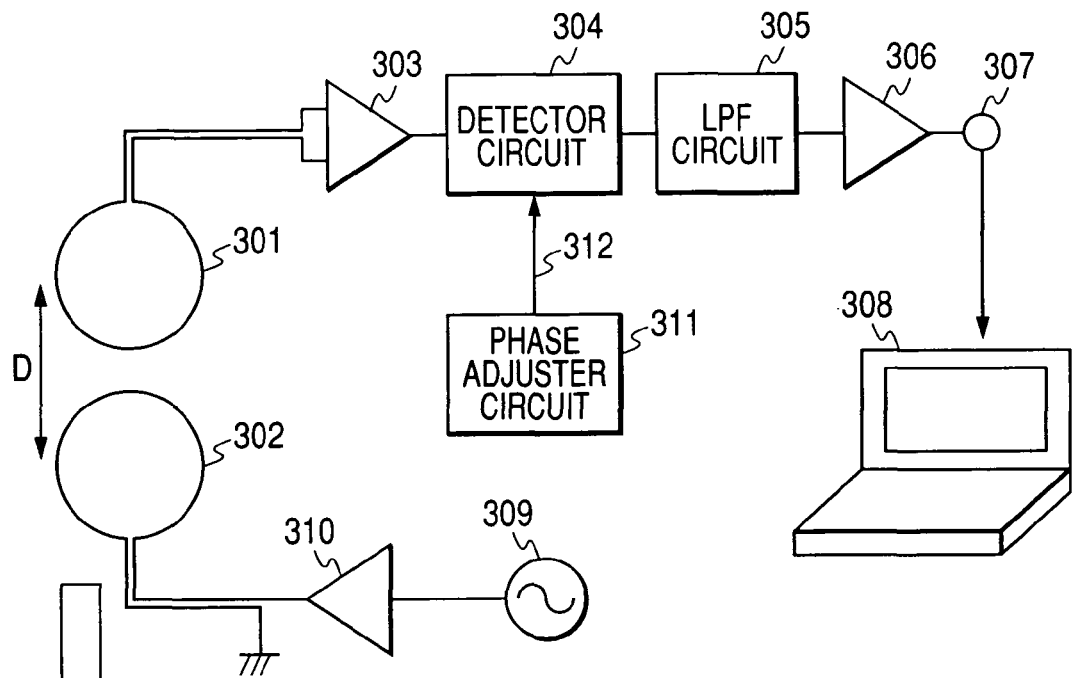
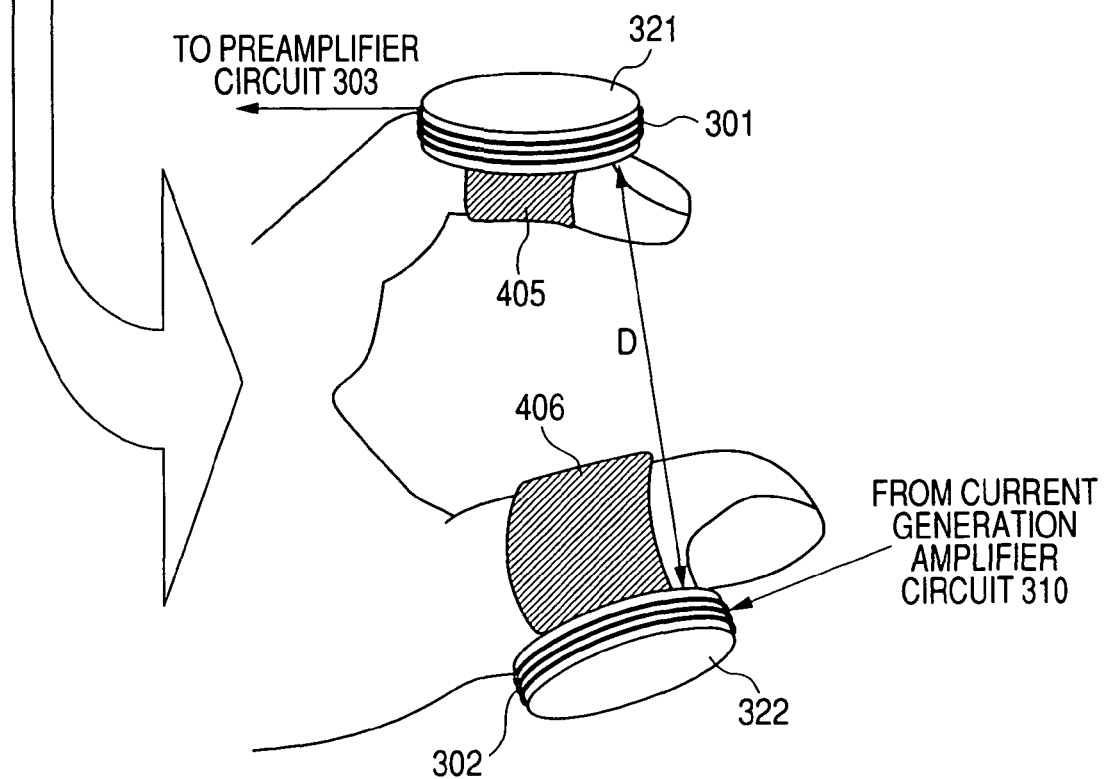

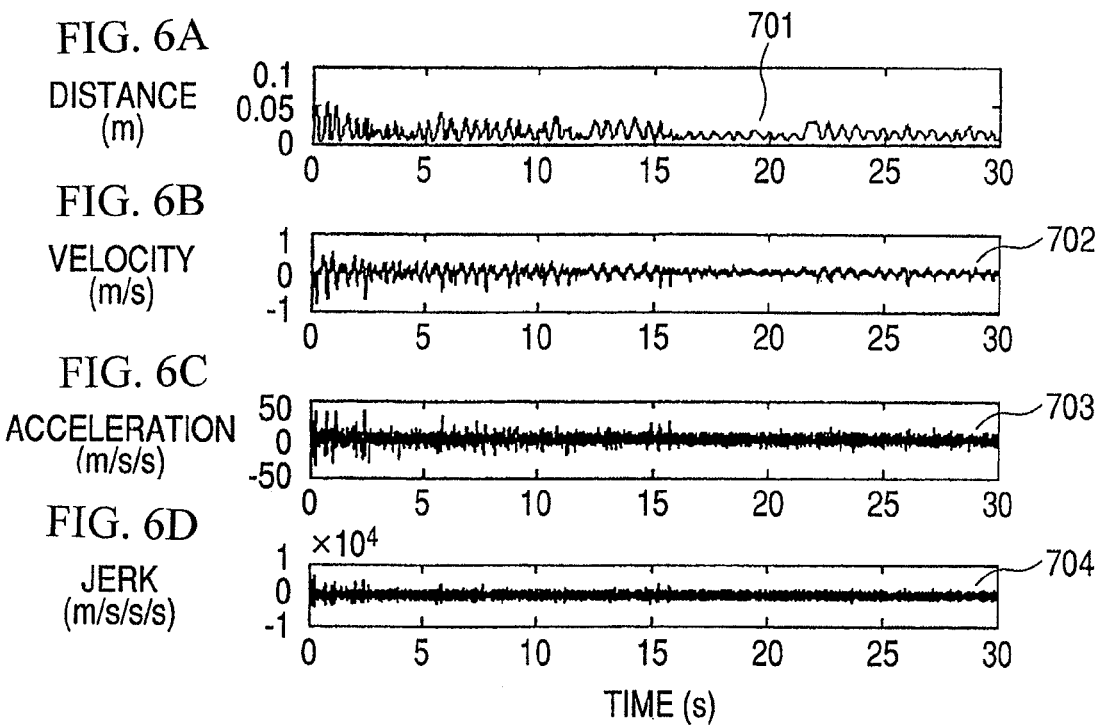
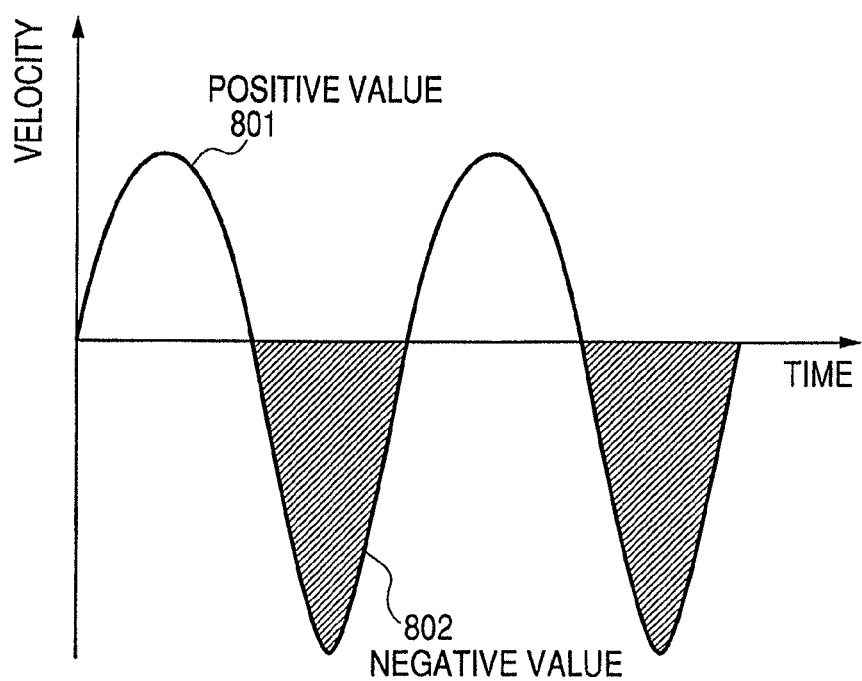

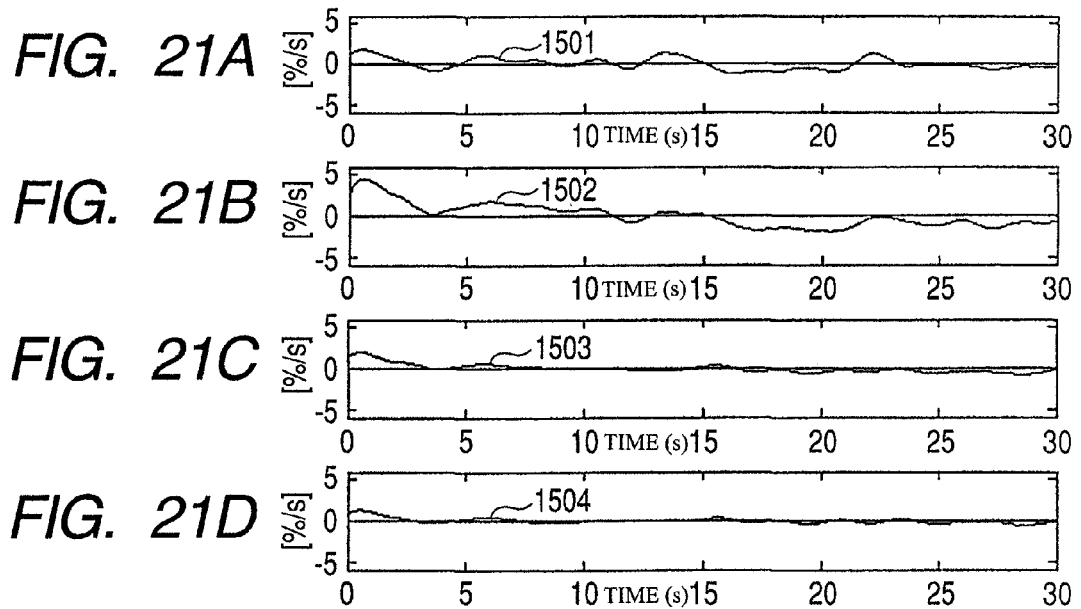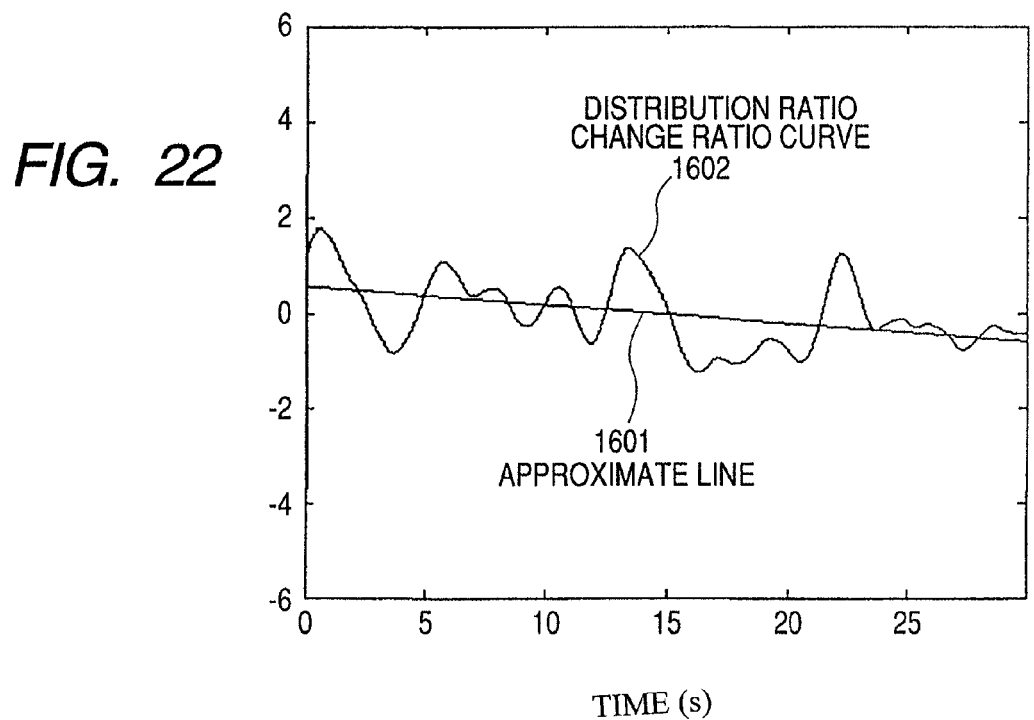

MOVEMENT ANALYSIS DISPLAY APPARATUS AND MOVEMENT ANALYZING METHOD

CLAIM OF PRIORITY

The present application claims priority from Japanese application JP 2005-120584 filed on Apr. 19, 2005, the content of which is hereby incorporated by reference into this application.

BACKGROUND OF THE INVENTION

The present invention relates to an apparatus for displaying movement information, and more particularly to an apparatus that analyzes a movement waveform that is acquired by a movement sensor, and displays quantitative movement information.

The Parkinson's disease is an incurable disease that a lesion develops in a substantial nigra or striate body within brains which control a movement, and causes ataxia of involuntary movement such as walking. Also, since it is a progressive disease, when the Parkinson's disease is untreated for about ten years, they say that a patient becomes bedridden. Thus, early diagnostic and treatment have been demanded.

However, the Parkinson's disease cannot be diagnosed by a blood test or diagnostic imaging regardless of a brain disease, and in the current state, the severity (progression stage) of the disease state is determined according to specific clinical manifestations (tremor, muscular rigidity, akinesia, pause retaining disorder, etc.) and patient's complaint. In the above determining method, it is difficult to quantitatively evaluate the severity of the disease state, and information for realizing appropriate medications is not satisfactory.

Up to now, in order to quantitatively evaluate the severity of the Parkinson's disease, a method of tapping the keyboard of a computer has been frequently studied (for example, refer to Movement Disorder vol. 15, No. 1, 2000, pp. 36 to 47). According to this method, the movement of a patient's fingers can be simply evaluated as on and off states.

Also, as another method, there is disclosed a manner in which a device for depressing a button is simply structured as with the keyboard, and a timing at which the button is depressed is measured (for example, refer to U.S. Pat. No. 6,416,485 B1). According to this method, the movement of a patient's fingers can be evaluated as on and off states as with the evaluation using the keyboard.

In addition, in the field of an input device for sign language, there is disclosed a method in which a primary winding is first excited, and a movement is detected by an arrangement of a magnetic response member and a secondary winding, to thereby evaluate the hooking and stretching of fingers (for example, refer to JP 2003-15810A). That is, in the invention disclosed in JP 2003-15810A, a transmitter coil is disposed in each of the fingers, and a receiver coil is disposed on a palm of the hand. Then, an AC current different in frequency is allowed to flow in each of the transmitter coils, and an induced electromotive force that has been obtained by the receiver coil on the palm of the hand is detected by a frequency detector circuit to detect which finger comes in contact with the palm.

Those three methods can acquire the movement of the fingers as digital on/off information.

On the other hand, as a method of evaluating the movement of fingers in an analog fashion, there has been reported a method of detecting the movement of fingers from an image obtained by a camera, which is called "optoelectronic camera system" (for example, refer to Movement disorder vol. 12, No. 5, 1997, pp. 665 to 676). According to the above method, the movement of fingers can be accurately detected.

Also, in the field of a metal detecting apparatus, as a method of detecting a metal substance that moves between a fixed exciting circuit and a detection coil, there is disclosed a method in which a variation of an eddy current that is detected by the detection coil is detected by a detector circuit, and the metal substance is detected through a low pass filter (for example, refer to JP Hei 5-5784A). According to the above method, the movement of the metal substance can be monitored.

In addition, the present inventors have discloses a magnetic sensor type finger tapping measuring device as a movement sensor that appropriately measures waveform data (for example, refer to Neurosci. Res. vol. 49, No. 2, 2004, pp. 253 to 260). That is, the device disclosed in the above publication is designed such that a coil that transmits a magnetic field of a high frequency (20 kHz) and a coil that receives the high frequency are put on fingers, an induced electromotive force of the high frequency magnetic field is detected by the receiver coil, detection is conducted by the frequency of the high frequency magnetic field, and filtering is conducted. Thereafter, recording is conducted as a digital signal by an AD converter of a notebook computer.

Those three methods can acquire the movement of fingers as analog information.

SUMMARY OF THE INVENTION

However, according to the inventions disclosed in U.S. Pat. No. 6,416,485 B1, JP 2003-15810, and Movement Disorder (vol. 15, No. 1, 2000, pp. 36 to 47), there can be acquired nothing other than digital information of on/off with respect to the movement of fingers, thereby making it impossible to sufficiently determine the poorness of the movement of fingers which is the specific symptom of the Parkinson's disease.

Also, according to the invention disclosed in Movement disorder vol. 12 (No. 5, 1997, pp. 665 to 676), there arises such problems that the apparatus is increased in size, and it takes time to analyze data.

Also, according to the invention disclosed in JP Hei 5-5784A, the movement of a biological body cannot be detected although the movement of metal can be detected.

Also, according to the invention disclosed in Neurosci. Res. Vol. 49 (No. 2, 2004, pp. 253 to 260), although the poorness of the movement of fingers which is the specific symptom of the Parkinson's disease can be appropriately detected by the measured waveform data, it is more preferable that the measured movement waveform can be quantitatively evaluated.

Under the above circumstances, an object of the present invention is to provide a movement analysis display apparatus that can quantitatively evaluate acquired movement information regardless of the type of a movement sensor.

To achieve the above object, according to the present invention, there is provided a movement analysis display apparatus, including: analyzing means for analyzing waveform data of a time series which is acquired from a movement sensor; and display means for displaying an analysis result that is analyzed by the analyzing means, wherein the analyzing means includes movement waveform generating means for generating a movement waveform corresponding to the waveform data from the waveform data to generate a velocity waveform from the movement waveform; and energy balance value calculating means for calculating a movement energy ratio in opposed movement directions by using a positive velocity value and a negative velocity value which constitute the velocity waveform.

With the above structure, a patient that suffers from the brain disorder such as the Parkinson's disease is compared with a healthy subject in an energy balance value calculated on the basis of the velocity waveform.

In addition, according to the present invention, there is provided a movement analysis display apparatus including: analyzing means for analyzing waveform data of a time series that is acquired from a movement sensor; and display means for displaying an analysis result that is analyzed by the analyzing means, wherein the analyzing means includes movement waveform generating means for generating a movement waveform corresponding to the waveform data from the waveform data to generate a distance waveform from the movement waveform, and envelope curve generating means for generating an envelope curve at a given time width in the distance waveform.

With the above structure, the envelope curve can be generated in the distance waveform, and the trend analysis of the distance waveform can be conducted by the characteristic of the envelope curve. As a result, for example, it is possible to evaluate the state of "deadlock" where the movement of a subject cowers as a time elapses.

Further, according to the present invention, there is provided a movement analysis display apparatus, including: analyzing means for analyzing waveform data of a time series that is acquired from a movement sensor; and display means for displaying an analysis result that is analyzed by the analyzing means, wherein the analyzing means includes movement waveform generating means for generating a movement waveform corresponding to the waveform data from the waveform data to generate a distance waveform from the movement waveform, and hour integration curve generating means for time-integrating the movement waveform.

With the above structure, the time integration curve can be generated in the movement waveform, and whether the movement of the subject is uniformly conducted or not, and an attainment energy that has been achieved by the subject can be evaluated by extracting the feature of the time integration curve.

Other features of the present invention will become apparent from the present specification.

According to the present invention, there can be provided a movement analysis display apparatus that is capable of quantitatively evaluating the acquired movement information regardless of the type of the movement sensor.

These and other objects and advantages of this invention will become more fully apparent from the following detailed description taken with the accompanying drawings in which:

FIG. 2 is a block diagram showing an example of the structure of a movement sensor according to the first embodiment;

FIGS. 6A-6D are graphs showing four types of movement waveforms which are generated by movement waveform generating means;

FIG. 7 is a partially enlarged diagram showing a velocity waveform;

FIGS. 21A to 21D are diagrams showing distribution ratio change rate curves, respectively;

FIG. 22 is a graph showing an approximate line into which the distribution ratio change rate curve based on the distance waveform is linearly approximated.

DETAILED DESCRIPTION OF THE PREFERRED EMBODIMENTS

Hereinafter, a description will be given in more detail of the preferred embodiments of the present invention with reference to the accompanying drawings.

First Embodiment

A first embodiment will be described. In the first embodiment, a movement is analyzed on the basis of a movement energy.

Figure 1:
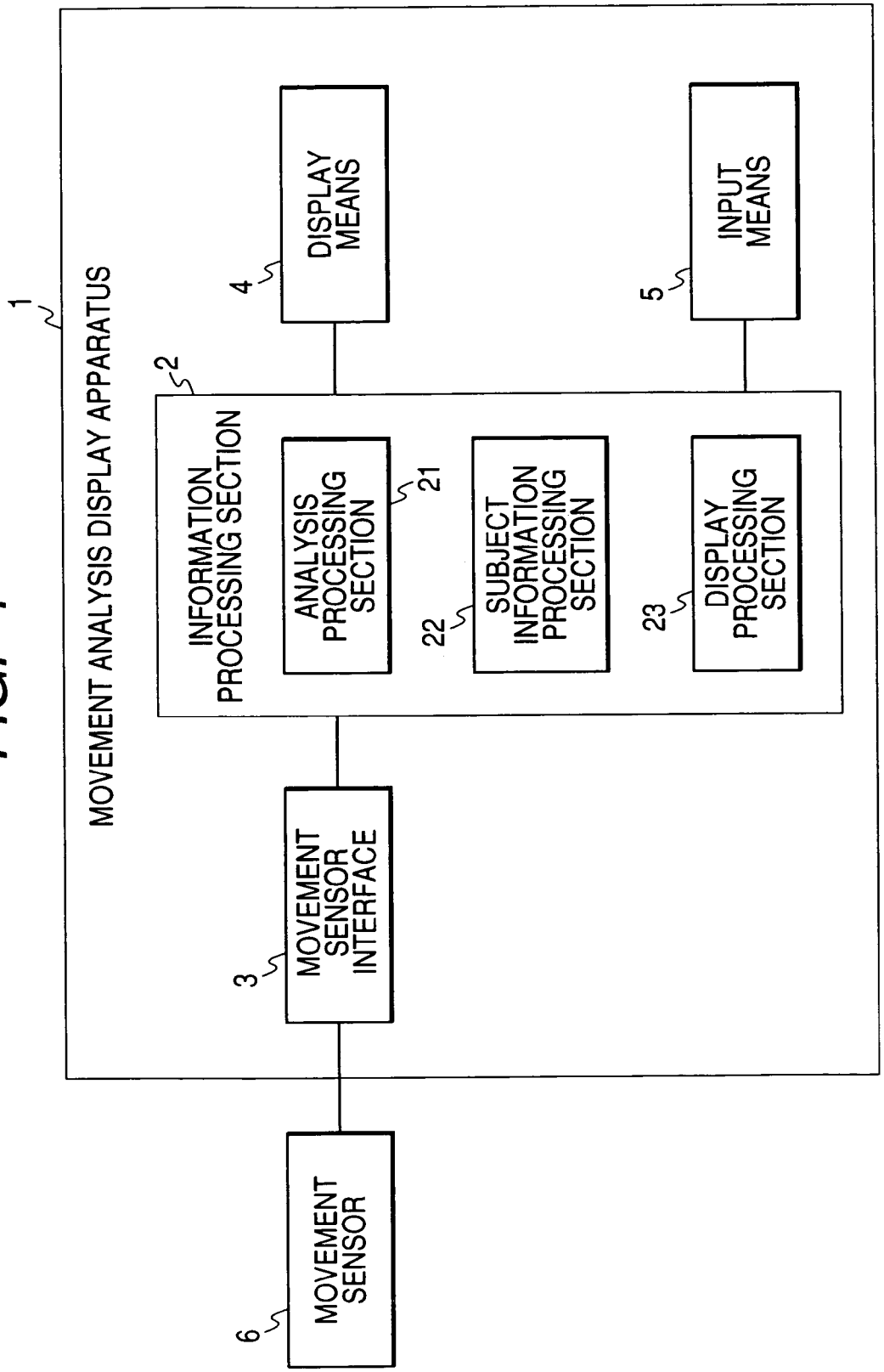
FIG. 1 is a block diagram showing the entire structure of a movement analysis display apparatus according to a first embodiment of the present invention.

FIG. 1 is a block diagram showing the entire structure of a movement analysis display apparatus according to a first embodiment. As shown in FIG. 1, a movement analysis display apparatus 1 includes an information processing section 2, a movement sensor interface 3, display means 4, and input means 5.

A movement sensor 6 that acquires the movement information of a subject as waveform data is connected to the movement analysis display apparatus 1 through a movement sensor interface 3.

In this example, the "subject" is an object to be measured by the movement sensor 6 which moves such as a machine, an animal, or a human.

Then, in this embodiment, it is assumed that the subject is a Parkinson's patient so far as there is no specific description.

The movement sensor 6 detects the movement information of the subject in time series, and acquires the movement information of the subject related to at least any one of a distance, a velocity, acceleration, and a jerk as waveform data.

FIG. 2 is a block diagram showing an example of the structure of the movement sensor 6 according to this embodiment. As shown in FIG. 2, the movement sensor 6 is structured by, for example, a magnetic sensor type tapping device disclosed in the above-mentioned "Neurosci. Res. Vol. 49, No. 2, 2004, pp. 253 to 260". Referring to FIG. 2, a transmitter coil 302 is worn on a lower portion of a thumb, and a receiver coil 301 is worn on an upper portion of a forefinger. The transmitter coil 302 is wound on a coil attachment member 322, and connected to a current generation amplifier 310. The receiver coil 301 is wound on a coil attachment member 321, and connected to a preamplifier circuit 303.

Then, an AC voltage having a specific frequency (for example, 20 kHz, etc.) is developed by an AC generator circuit 309. The AC voltage having the specific frequency which has been developed by the AC generator circuit 309 is converted into an AC current having a specific frequency by the current generation amplifier circuit 310. The AC current that has been developed by the current generation amplifier circuit 310 is allowed to flow in the transmitter coil 302. A magnetic field that has been developed by the transmitter coil 302 develops an induced electromotive force within the receiver coil 301.

The developed induced electromotive force (having the same frequency as that of the AC voltage having the specific frequency which has been developed by the AC generator circuit 309) is amplified by the preamplifier circuit 303, and a signal that has been amplified is inputted to a detector circuit 304.

In the detector circuit 304, because detection is conducted by a specific frequency or twice frequency which has been generated by an AC generator circuit 309, an output of the AC generator circuit 309 is connected to a reference signal input terminal of the detector circuit 304 as a reference signal 312 after being adjusted in phase by a phase adjuster circuit 311.

Also, in the case of conducting detection by twice frequency of the specific frequency, the phase adjuster circuit 311 is not always required. As a simple circuit structure that conducts detection by the twice frequency, the specific frequency of the AC generator circuit 309 is set to a twice frequency, and after the frequency has been converted into the half frequency by a divider, the frequency is inputted to the current generation amplifier circuit 310. The signal having the twice frequency of the specific frequency of the AC generator circuit 309 is connected to the reference signal input terminal of the detector circuit 304 as the reference signal 312.

The output of the detector circuit 304 passes through an LPF (low-pass filter) circuit 305, and is then amplified by the amplifier 306 in order to obtain a desired voltage, to thereby obtain an output 307.

An output 307 is inputted to a computer 308 as digital data by an analog to digital converter board (AD board) built in a computer 8.

With the above structure, a voltage corresponding to a relative distance D of the receiver coil 301 and the transmitter coil 302 which are worn on a biological object appears in the output 307.

In this embodiment, an instruction is given the subject to conduct the tapping movement where the forefinger and the thumb are superimposed on each other as quickly as possible for 30 seconds.

Then, the movement sensor 6 acquires the movement at this time as waveform data corresponding to the distance waveform.

Also, the fingers that wear the receiver coil 301 and the transmitter coil 302 are not limited to the thumb and the forefinger, but the receiver coil 301 and the transmitter coil 302 may be attached to any fingers. Also, a case in which the finger may be attached onto the detector coil is given with reference to FIG. 2. However, the transmitter coil 302 and the receiver coil 301 may be attached onto an upper lip and a lower lip so that the movement accompanied by the movement of a mouse may be detected. Also, the transmitter coil 302 and the receiver coil 301 may be attached onto upper and lower portions of an eye to detect blinking and the movement of eyelids.

The movement sensor 6 that acquires the movement information of the subject as the waveform data is not limited to the tapping device thus structured, but any structure may be applied if the movement information can be acquired as the waveform data.

For example, the movement sensor 6 may be structured by a movement sensor such as a known strain gauge, acceleration meter, or velocity meter, or may be structured by a movement sensor that acquires the movement information on the subject by image analysis.

Returning to FIG. 1, the description of the movement analysis display apparatus 1 continues.

A movement sensor interface 3 includes, for example, an analog digital converter board (hereinafter referred to as "AD board") provided in a general computer, converts the waveform data of an analog signal that has been detected by the movement sensor 6 into the waveform data of the digital signal at a given sampling frequency, and inputs the waveform data to the information processing section 2 of the movement analysis display apparatus 1.

Display means 4 displays subject information or movement information which has been processed by the information processing section 2, and can be realized by, for example, an LCD (liquid crystal display) display, or a CRT (cathode ray tube) display.

Also, the input means 5 is so disposed as to input the subject information by an operator of the movement analysis display apparatus 1 not shown, and can be realized by a keyboard or a mouse. Also, in the case of inputting the subject information, an input screen may be displayed on the display means 4 as a user interface that assists an operator's input.

The information processing section 2 analyzes the waveform data that has been acquired by the movement sensor 6, extracts the feature quantity of movement, and appropriately displays the extracted feature quantity together with the subject information on the display means 4.

In this example, the information processing section 2 includes an analysis processing section 21, a subject information processing section 22, and a display processing section 23.

The information processing section 2 includes a CPU (central processing unit), a memory that is made up of a ROM (read only memory) or a RAM (random access memory), and a hard disk. The respective processing sections 21 to 23 within the information processing section 2 correspond to a program or data which is stored in the memory or the hard disk. Then, the CPU reads program from the memory and executes the arithmetic processing, to thereby realize the respective processing of the information processing section 2.

(Analysis Processing Section)

Figure 3:
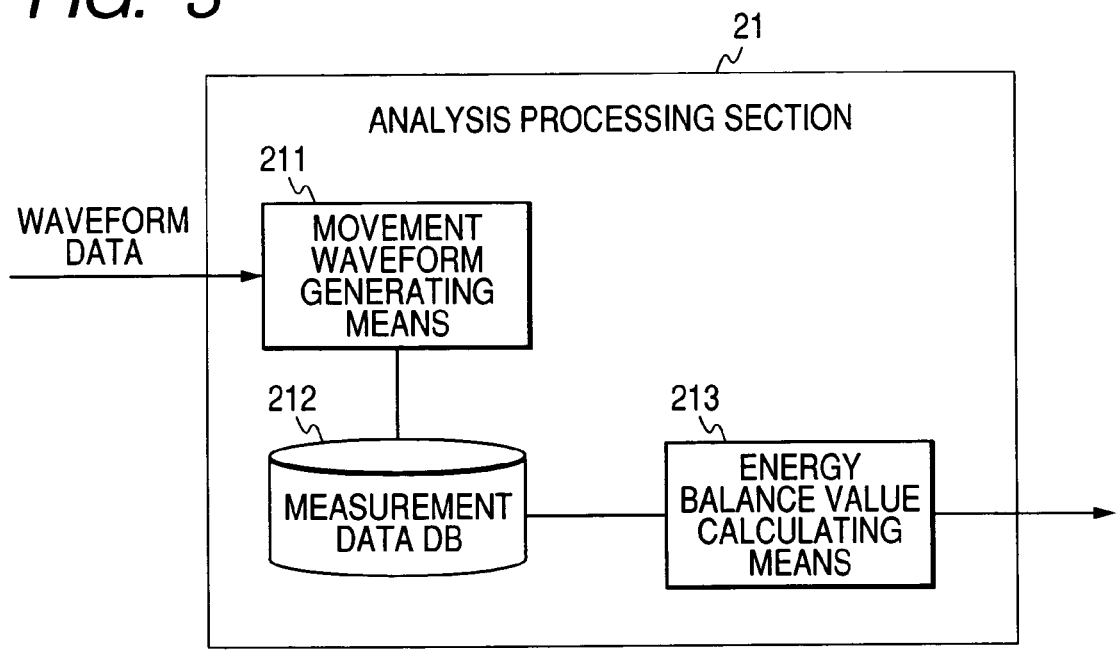
FIG. 3 is a block diagram showing the structure of an analysis processing section according to the first embodiment.

FIG. 3 is a block diagram showing the structure of an analysis processing section 21 according to the first embodiment. As shown in FIG. 3, the analysis processing section 21 extracts the feature quantity of movement on the basis of the waveform data inputted from the movement sensor 6. Then, the result that has been analyzed by the analysis processing section 21 is recorded in a subject DB not shown which is disposed in the subject information processing section 22, appropriately read from the subject DB by the display processing section 23, and displayed on the display means 4.

In this example, the analysis processing section 21 of the first embodiment includes movement waveform generating means 211, measurement data DB (database) 212, and energy balance value calculating means 213.

The measurement data DB can be realized by a memory or a hard disk.

[Movement Waveform Generating Means]

The waveform data that has been acquired from the movement sensor 6 does not directly express the movement waveform, but expresses a voltage output corresponding to the movement waveform.

The movement waveform generating means 211 converts the waveform data that is the voltage data into a corresponding movement waveform, and generates a distance waveform, a velocity waveform, an acceleration waveform, and a jerk waveform on the basis of the converted movement waveform in a complementary manner.

The "movement waveform" includes at least one of the distance waveform, the velocity waveform, the acceleration waveform, and the jerk waveform so far as there is no specific limit.

In this example, a procedure of generating four types of movement waveforms from the waveform data by the movement waveform generating means 211 will be described with reference to FIG. 4.

Figure 4:
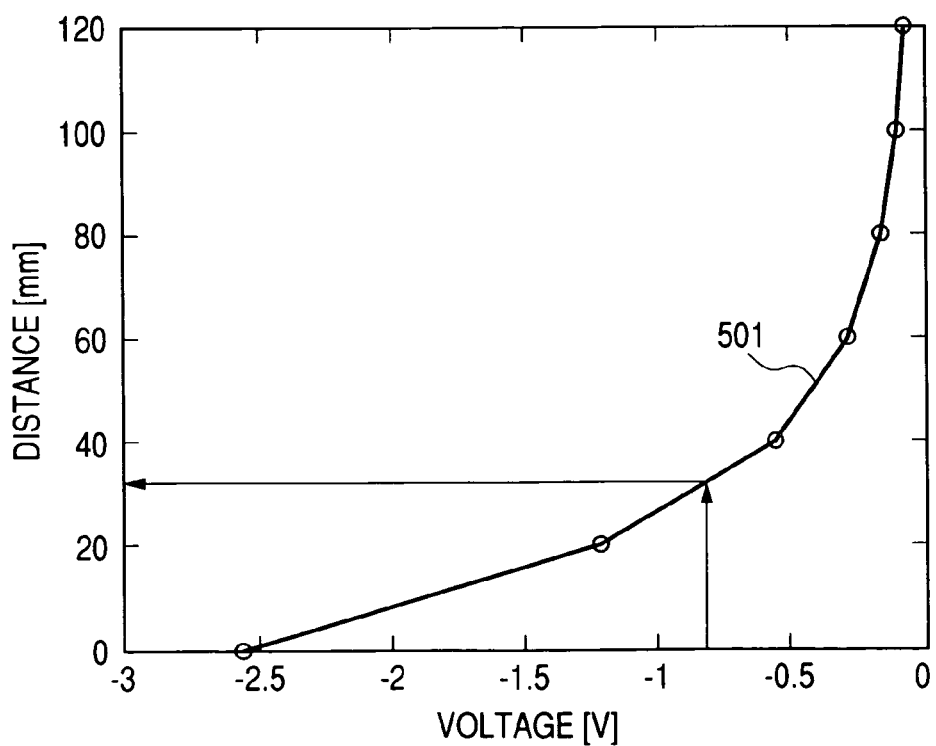
FIG. 4 is a graph showing a voltage to distance conversion line for converting waveform data of a voltage output that is acquired from the movement sensor according to the first embodiment.

FIG. 4 is a graph showing a voltage to distance conversion line for converting the waveform data of the voltage output that has been acquired from the movement sensor 6 of this embodiment into a distance waveform. A voltage to distance conversion line 501 shown in FIG. 4 is stored in a hard disk in advance, and read in the memory by the movement waveform generating means 211.

First, the movement waveform generating means 211 collinear approximates the waveform data in each of sections and converts the approximated data into a distance value. Also, a voltage value out of the sections can be obtained by using a line in an adjacent section as it is.

Figure 5A:
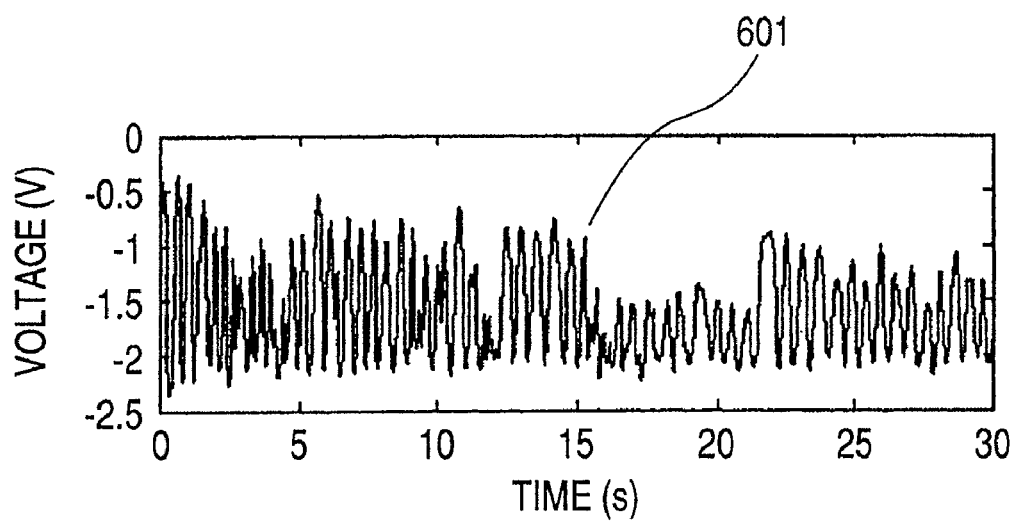
FIGS. 5A-5B are graphs showing waveform data of a voltage output that has not been converted and waveform data of a voltage output that has been converted.
Figure 5B:
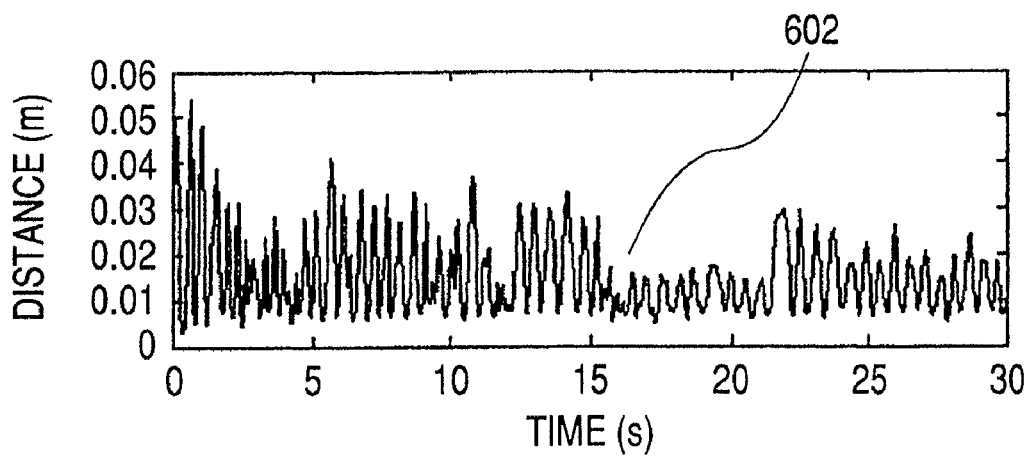

FIGS. 5A-5B are graphs showing the waveform data of the voltage output that has not yet been converted and the distance waveform that has been converted. As shown in FIGS. 5A-5B, a distance waveform 602 is different in the configuration of the waveform from the waveform data 601. In order to appropriately quantitatively analyze the movement waveform, a converting process due to the movement waveform generation converting means 31 is effective.

Then, the distance waveform 602 thus converted is recorded in the measurement data DB 212.

Subsequently, the movement waveform generating means 211 complementarily generates another movement waveform that has not been recorded in the measurement data DB 212 on the basis of the movement waveform that has been recorded in the measurement data DB 212. More specifically, in the case where only the distance waveform is recorded in the measurement data DB 212, the movement waveform generating means 211 reads the distance waveform from the measurement data DB 212 and differentiates the distance waveform with respect to time, to there by generate the velocity waveform. The generated velocity waveform is recorded in the measurement data DB 212. The acceleration waveform is similarly generated by differentiating the velocity waveform with respect to the time by the movement waveform generating means 211, and the jerk waveform is also generated by differentiating the acceleration waveform with respect to the time by the movement waveform generating means 211. Then, the movement waveform generating means 211 records the respective generated movement waveforms in the measurement data DB 212.

As in this embodiment, in the case where the distance waveform is sequentially differentiated with respect to the time to generate another movement waveform, the movement waveform generating means 211 can obtain the velocity waveform, the acceleration waveform, and the jerk waveform using the following expressions (1) to (3), respectively.

$$\text{Velocity } (n\text{-}th) = [\text{distance } (n+1\text{-}th) - \text{distance } (n\text{-}th)] \times \text{sampling frequency} \quad (1)$$

$$\text{Acceleration } (n\text{-}th) = [\text{velocity } (n+1\text{-}th) - \text{velocity } (n\text{-}th)] \times \text{sampling frequency} \quad (2)$$

$$\text{Jerk } (n\text{-}th) = [\text{acceleration } (n+1\text{-}th) - \text{acceleration } (n\text{-}th)] \times \text{sampling frequency} \quad (3)$$

FIGS. 6A-6D show the distance waveform that has been converted from the waveform data, and other movement waveforms that have been generated on the basis of the distance waveform.

FIGS. 6A-6D show four types of movement waveforms that have been generated by the movement waveform generating means 211.

As described above, because it is possible to generate four types of movement waveforms related to a distance waveform 701, a velocity waveform 702, an acceleration waveform 703, and a jerk waveform 704 can be generated on the basis of at least one of those movement waveforms, the movement of the subject can be analyzed from more various perspectives. More particularly, the jerk waveform 704 that is applied in this embodiment is suitable in evaluation of "awkwardness" of the movement of the subject.

Also, as another example, in the case where the acceleration meter that is generally used is used as a movement sensor, the waveform data of the voltage output that has been detected by the acceleration meter is converted into the acceleration waveform by the movement waveform generating means 211. Then, the acceleration waveform is differentiated with respect to time by using the above expression (3) to acquire the jerk waveform. On the other hand, the acceleration waveform is sequentially integrated with respect to time, thereby making it possible to acquire the velocity waveform and the distance waveform. The calculation expression that is applied to the time integration can be readily led from the above expressions (1) to (3).

Likewise, even in the case where a storage gauge or a speed meter is applied as the movement sensor 6 and even in the case where the movement sensor 6 extracts movement information from image data, when at least one movement waveform is measured, the differentiation and integration are conducted, thereby making it possible to complementarily obtain other movement waveforms (distance, velocity, acceleration, jerk).

[Energy Balance Value Calculating Means]

The energy balance value calculating means 213 calculates an energy balance value in order to evaluate the energy balance of movement in opposite directions in the velocity waveform.

Now, a description will be given of a procedure of calculating the energy balance value by the energy balance value calculating means 213 with reference to FIG. 7.

FIG. 7 is a partially enlarged diagram showing the velocity waveform. In the velocity waveform shown in FIG. 7, the axis of ordinate (Y axis) is a velocity, and the axis of abscissas (X axis) is a time. The velocity waveform can be divided into a positive velocity waveform and a negative velocity waveform with a boundary of the X axis (velocity=0)

First, the energy balance value calculating means 213 can obtain the second-power integration value of the positive velocity value (positive value) and the second-power integration value of the negative velocity value (negative value) in the velocity waveform.

In this example, the energy balance value calculating means 213 can obtain the second-power integration value of the positive velocity value (positive value) and the second-power integration value of the negative velocity value (negative value) in the velocity waveform by using the following expressions (4) and (5), respectively.

$$[\text{Second-power integration value of positive value}]=\Sigma \\ [\text{velocity } (n) \times \text{velocity } (n)]/\text{sampling frequency} \quad (4)$$

(a case of velocity (n)≧0)

$$[\text{Second-power integration value of negative value}]=\Sigma \\ [\text{velocity } (m) \times \text{velocity } (m)]/\text{sampling frequency} \quad (5)$$

(A case of velocity (m)≦0)

In this example, the reason that the second-power integration value is applied is because the movements in different directions are readily compared with each other since the calculated values are always positive, and the comparison of values obtained by calculating the second power of the velocity values readily corresponds to the comparison of the movement energies.

Subsequently, the ratio of the second-power integration values is calculated. The ratio of the second-power integration values can be obtained by the following expression (6).

$$[\text{Energy balance value}]=[\text{second-power integration} \\ \text{value of positive value}]/[\text{second-power integration value of negative value}] \quad (6)$$

In this embodiment, the energy balance value is calculated after the second-power integration values of the positive value and the negative value of the entire measurement time (30 seconds) are obtained, respectively. However, it is not always necessary to conduct the integration and comparison in the entire measurement time. For example, it is possible that the second-power integration values of the positive value and the negative value in one cycle are calculated to obtain the energy balance. In addition, it is possible that a change in the energy balance in one cycle is calculated over the entire measurement time, and observed as a change curve of the energy balance value.

Thus, according to the energy balance value calculating means 213, the movement energy ratio in the positive and negative directions can be evaluated by calculating the energy balance value.

Incidentally, there has been known that it is difficult for the patient with the brain disorder such as the Parkinson's disease to conduct the movement in a direction of opening the fingers (positive direction) as compared with the movement in a direction of closing the fingers (negative direction). Also, there has been known that a difference in the movement in the negative direction is small between the patient and the healthy subject. Then, in the case where this embodiment is applied to the Parkinson's patient, a tendency is made that the energy balance value of the Parkinson's patient is smaller than that of the healthy subject.

Accordingly, this embodiment is preferable in evaluation of the severity of the patient with the brain disorder such as the Parkinson's disease.

(Subject Information Processing Section)

The subject information processing section 22 includes the subject DB not shown which records information such as the subject information and the analysis result, and manages the information that is recorded in the subject DB.

More specifically, in the case of conducting 1) the registration, correction, deletion, retrieval, and sort of the subject information, 2) association of the subject information with the measurement data, 3) registration, correction, and deletion (addition, correction, and deletion of items) of the analysis result of the measurement data, and 4) statistical processing, the subject information processing section 22 conducts the processing of main four items related to the registration, correction, and deletion of the statistical processing results in cooperation with the subject DB.

Also, as the subject information that is registered in the subject DB, there are subject ID, name, birth date, age, body height, body weight, disorder name, and comments on the subject.

Those information management made by the subject information processing section 22 can be readily realized by the conventional program and data configuration.

Also, the subject DB can be realized by a hard disk.

(Display Processing Section)

The display processing section 23 displays information such as the subject information or analysis result which has been registered in the subject DB on the display means 4 by approximately using the formats of graphs and tables which are visually understandable display formats.

The display processing section 23 does not need to display all of the above analysis results at the same time, and can display items that are appropriately selected by the operator.

Figure 8:
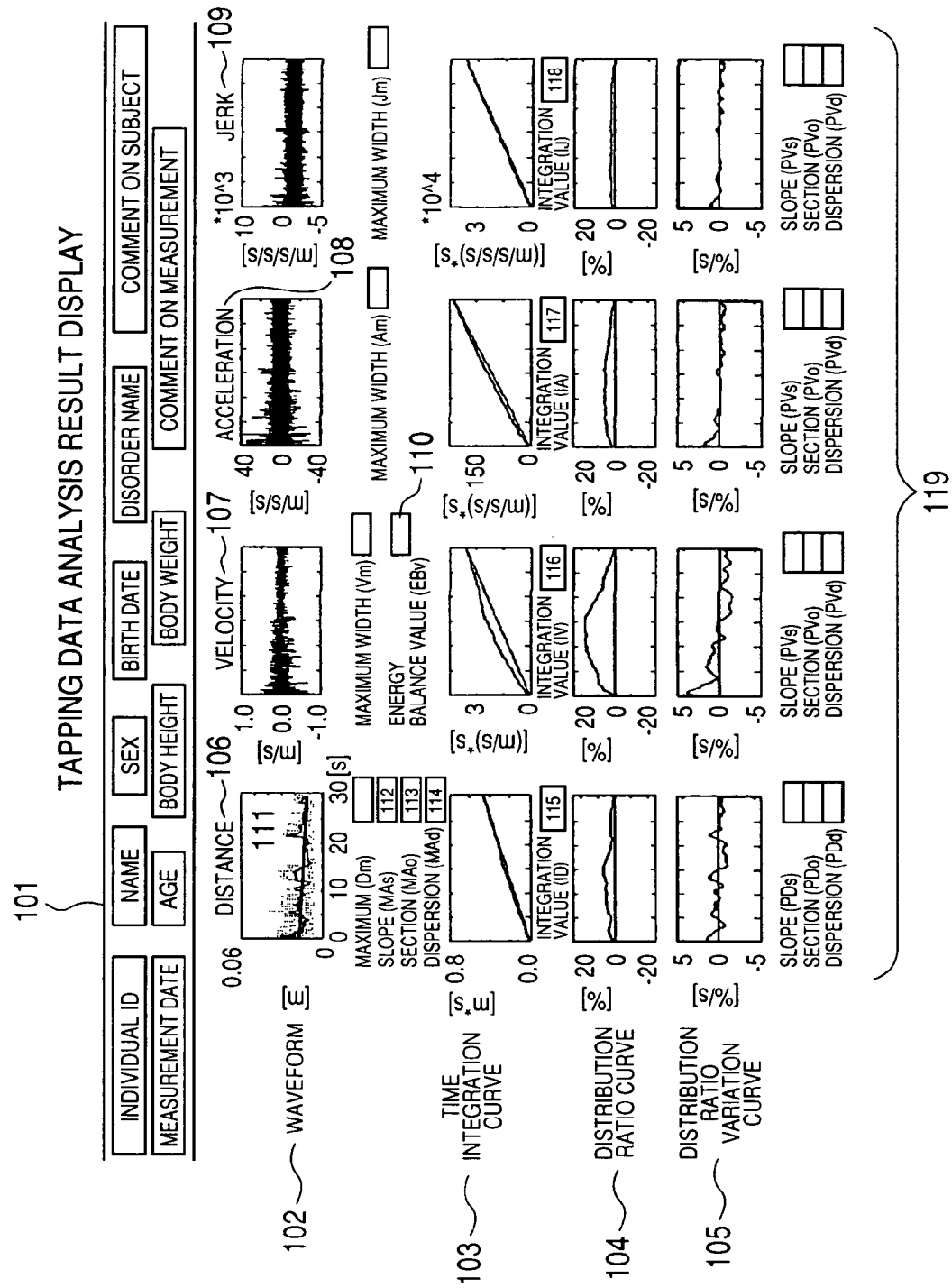
FIG. 8 is a diagram showing an example of a screen configuration that is displayed on display means.

FIG. 8 is a diagram showing an example of a screen configuration that is displayed on the display means 4 by the display processing section 23.

As shown in FIG. 8, on the display means 4 are displayed a subject information input column 101, a waveform analysis column 102, a time integration analysis column 103, a distribution ratio analysis column 104, and a distribution ratio change rate analysis column 105. Also, in the waveform analysis column 102, the time integration analysis column 103, the distribution ratio analysis column 104, and the distribution ratio change rate analysis column 105, the results of analyzing a distance waveform, a velocity waveform, an acceleration waveform, and a jerk waveform can be displayed, respectively.

As described above, the analysis result is displayed on the display means 4, to thereby obtain such an advantage that the movement function such as the movement of the fingers is quantitatively and visually understandable.

This embodiment is described with reference to a drawing showing data assuming the Parkinson's patient. In the case where the movement analysis display apparatus 1 according to this embodiment is applied to the healthy subject, for example, a tendency is made that a movement waveform curve large in amplitude and short in cycle (high in frequency) is displayed on the display means 4 as compared with the Parkinson's patient.

Also, a tendency is made that the energy balance value of the healthy subject is displayed on the display means 4 as a value relatively larger than that of the Parkinson's patient.

Second Embodiment

Now, a description will be given of a movement analysis display apparatus according to a second embodiment with reference to the drawings.

In the second embodiment, a movement is analyzed on the basis of an envelope curve generated in the distance waveform.

The second embodiment has a characteristic structure in an analysis processing section 21 within the information processing section 2. Accordingly, in the description of the second embodiment, partially the analysis processing section 21 will be described in more detail, but the duplicated description of the first embodiment will be omitted.

(Analysis Processing Section)

Figure 9:
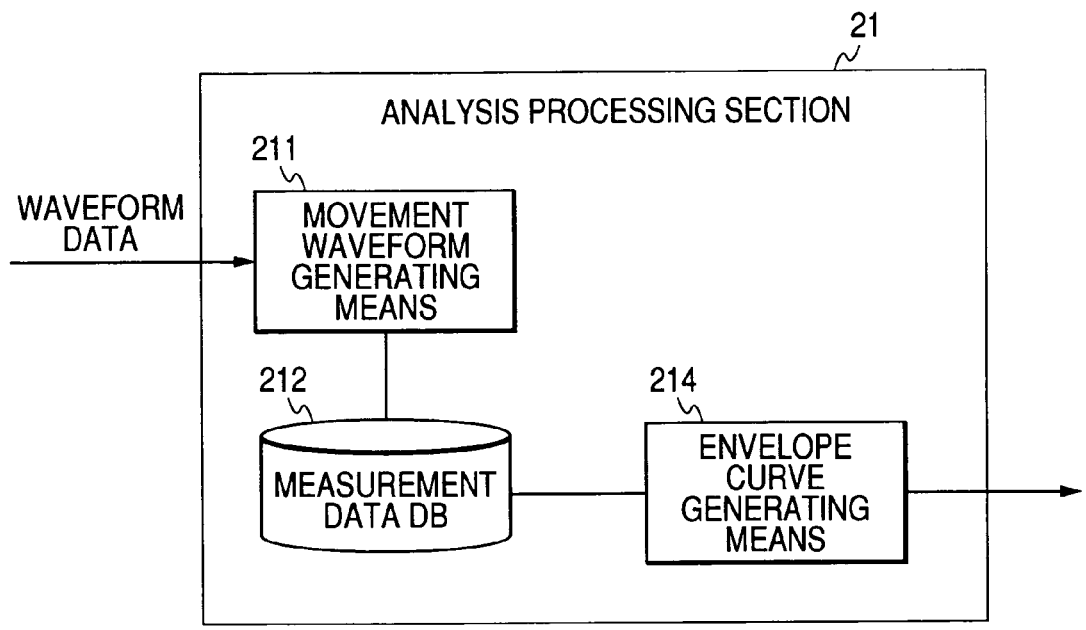
FIG. 9 is a block diagram showing the structure of an analysis processing section according to a second embodiment.

FIG. 9 is a block diagram showing the structure of the analysis processing section 21 according to the second embodiment.

In this embodiment, the analysis processing section 21 according to the second embodiment includes movement waveform generating means 211, measurement data DB 212, and envelope curve generating means 214.

[Envelope Curve Generating Means]

The envelop curve generating means 214 generates an envelope curve of a distance waveform in order to observe the overall movement of the opening degree of fingers of the distance waveform.

Figure 10:
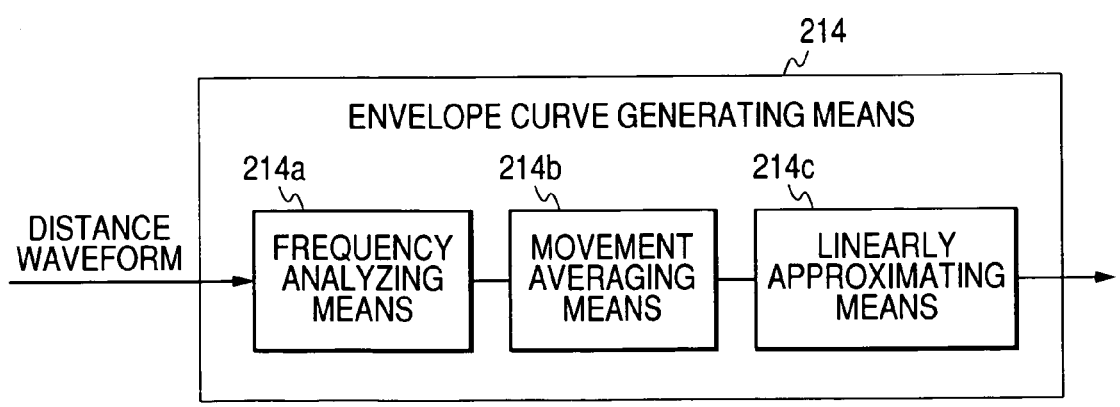
FIG. 10 is a block diagram showing the structure of envelope curve generating means according to the second embodiment.

FIG. 10 is a block diagram showing the structure of envelope curve generating means 214. As shown in FIG. 10, the envelope curve generating means 214 generates an envelope curve in the distance waveform (corresponding to a movement average wave that will be described later in this embodiment). Also, the envelope curve generating means 214 linearly approximates the envelope curve to conduct the trend analysis of the distance waveform.

In this embodiment, the envelope curve generating means 214 includes frequency analyzing means 214a, movement averaging means 214b, and linearly approximating means 214c.

<Frequency Analyzing Means>

The frequency analyzing means 214a conducts the frequency analysis of the distance waveform, calculates the maximum spectrum frequency value, and calculates a cycle T of its inverse.

Figure 11:
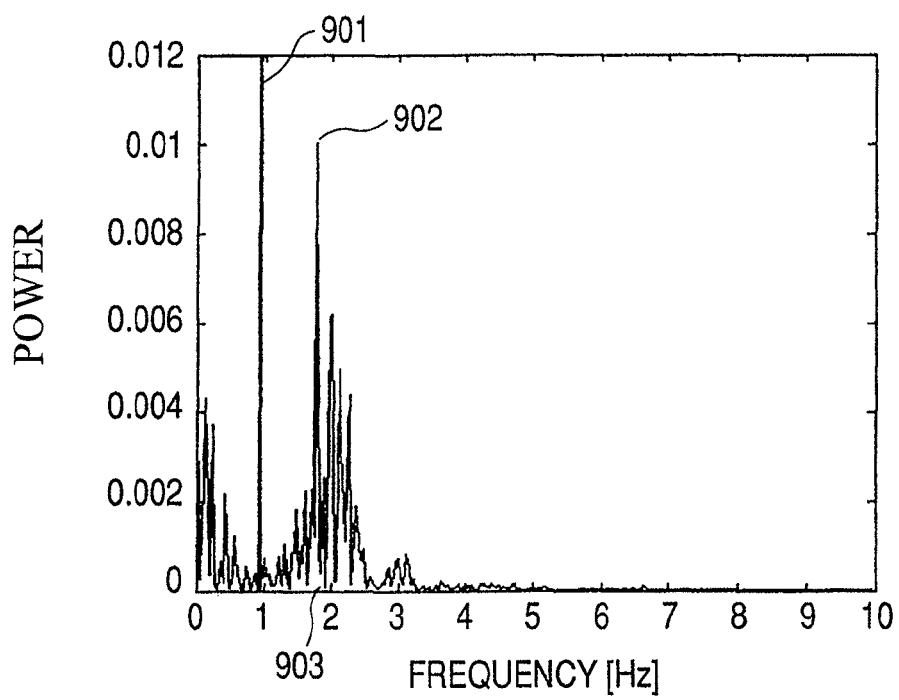
FIG. 11 is a graph showing a power spectrum that is generated by conducting digital Fourier transformation with respect to a distance waveform.

Now, a description will be given of a procedure of conducting the frequency analysis of the distance waveform by the frequency analyzing means 214a with reference to FIG. 11. FIG. 11 is a graph displaying a power spectrum that is generated by subjecting the distance waveform to digital Fourier transformation.

First, the frequency analyzing means 214a conducts digital Fourier transformation on the distance waveform to generate a power spectrum. The generated power spectrum is displayed as shown in FIG. 11, in which the axis of abscissa is indicative of a frequency whereas the axis of ordinate is indicative of a power.

Subsequently, the frequency analyzing means 214a extracts a maximum spectrum frequency value 903 which becomes a value 902 indicative of the maximum power in the power spectrum.

In this situation, the maximum spectrum frequency value 903 becomes a frequency that is equal to or higher than a threshold value 901 that is set by an operator in advance. The reason that the threshold value 901 is set is because the lower frequency components are mainly indicative of the slow fluctuation of the entire hand and get off a purpose of this embodiment which evaluates the open/close movement of fingers.

Then, the frequency analyzing means 214a obtains the inverse of the maximum spectrum frequency value 903, and calculates the cycle T. The frequency analyzing means 214a is capable of obtaining the cycle T of the maximum spectrum frequency value 903 by using the following expression (6).

$$\text{Cycle T=integer value[sampling frequency/maximum spectrum frequency value]} \qquad (6)$$

In this example, the cycle T of the distance waveform which has been calculated by the frequency analyzing means 214a is outputted to the movement averaging means 214b.

<Movement Averaging Means>

The movement averaging means 214b conducts the movement averaging process of the distance waveform at time widths of the cycle T and generates the movement average wave.

Now, a description will be given of a procedure of conducting the movement averaging process on the distance waveform and generating the movement average wave with reference to FIG. 12.

Figure 12:
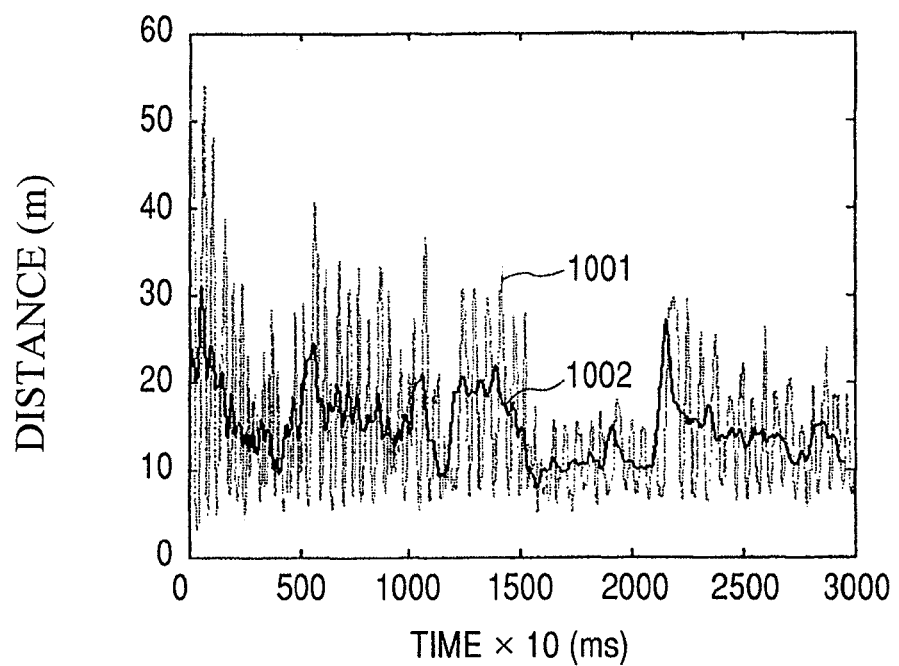
FIG. 12 is a graph showing a distance waveform that has been subjected to a movement averaging process.

In FIG. 12, the distance waveform is subjected to the movement averaging process.

The movement averaging means 214b can obtain the movement average wave 1002 from the distance waveform 1001 by using the following expression (7).

$$\text{Movement average wave }(n)=\text{average[distance}(n)\text{ to distance }(n+P-1)] \qquad (7)$$

In this example, the movement average wave 1002 that has been calculated by the movement averaging means 214b is outputted to the linearly approximating means 214c.

<Linearly Approximating Means>

The linearly approximating means 214c linearly approximates the movement average wave 1002 to generate the approximate line, and extracts the features of the approximate line.

Figure 13:
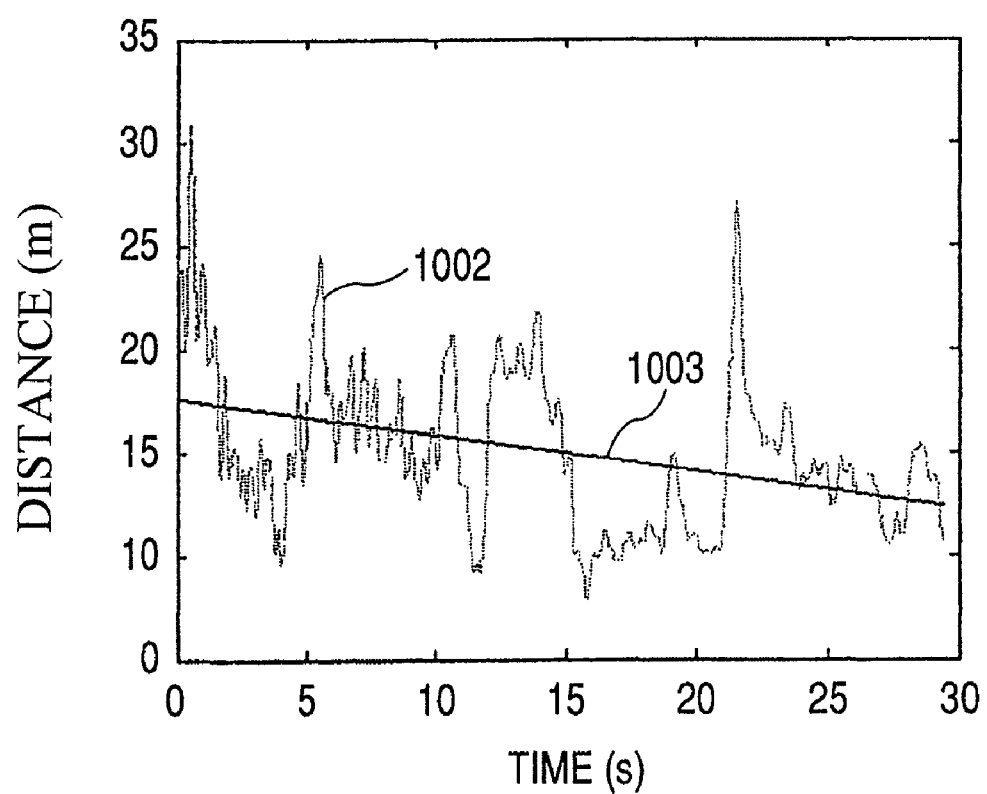
FIG. 13 is a diagram showing an approximate line into which a movement average wave is linearly approximated.

FIG. 13 is a diagram showing the approximate line resulting from linearly approximating the movement average wave. In FIG. 13, an approximate line 1003 is generated by linearly approximating a movement average wave 1002 by the linearly approximating means 214c. Then, when the approximate line 1003 is reduced with time, a tendency is made that the overall movement of the fingers is slowly reduced.

Then, the linearly approximating means 214c extracts the feature quantity of the generated approximate line 1003. The feature quantity of the extracted approximate line 1003 is, for example, a slope, a section, or a dispersion value from the approximate line 1003.

As described above, the linearly approximating means 214c is capable of quantitatively observing the tendency of the movement average wave 1002 by extracting the feature quantity of the approximate line 1003 resulting from linearly approximating the movement average wave 1002. Then, the tendency of the movement average wave 1002 that has been quantitatively observed quantitatively reflects the tendency of the distance waveform 1001.

As described above, the envelope curve generating means 214 generates the envelope curve (corresponding to the movement average wave in this embodiment), thereby being capable of analyzing the tendency of the distance waveform 1001.

In this embodiment, since the cycle T is set on the basis of the maximum spectrum frequency, and the movement average is taken by the time width of the cycle T, the envelope curve from which an influence of individual differences is removed can be produced.

The envelope curve generating means 214 according to this embodiment is preferable particularly in the case where the cutoff frequency should be changed per subject because the center frequency of the finger tapping is different in each of the subjects.

In this embodiment, the description is given with reference to the drawing showing data assuming the Parkinson's patient. However, in the case where the movement analysis display apparatus 1 according to the present invention is applied to the subject, for example, a tendency is made that the approximate line of the envelope curve that is low in the time reduction ratio and diffusion is displayed on the display means 4 as compared with the Parkinson's patient.

<Movement Analysis Method>

Subsequently, a description will be given of a movement analyzing method using the movement analysis display apparatus of this embodiment with reference to FIG. 14. The movement analyzing method in this embodiment uses a manner of generating the envelope curve in the distance waveform.

Figure 14:
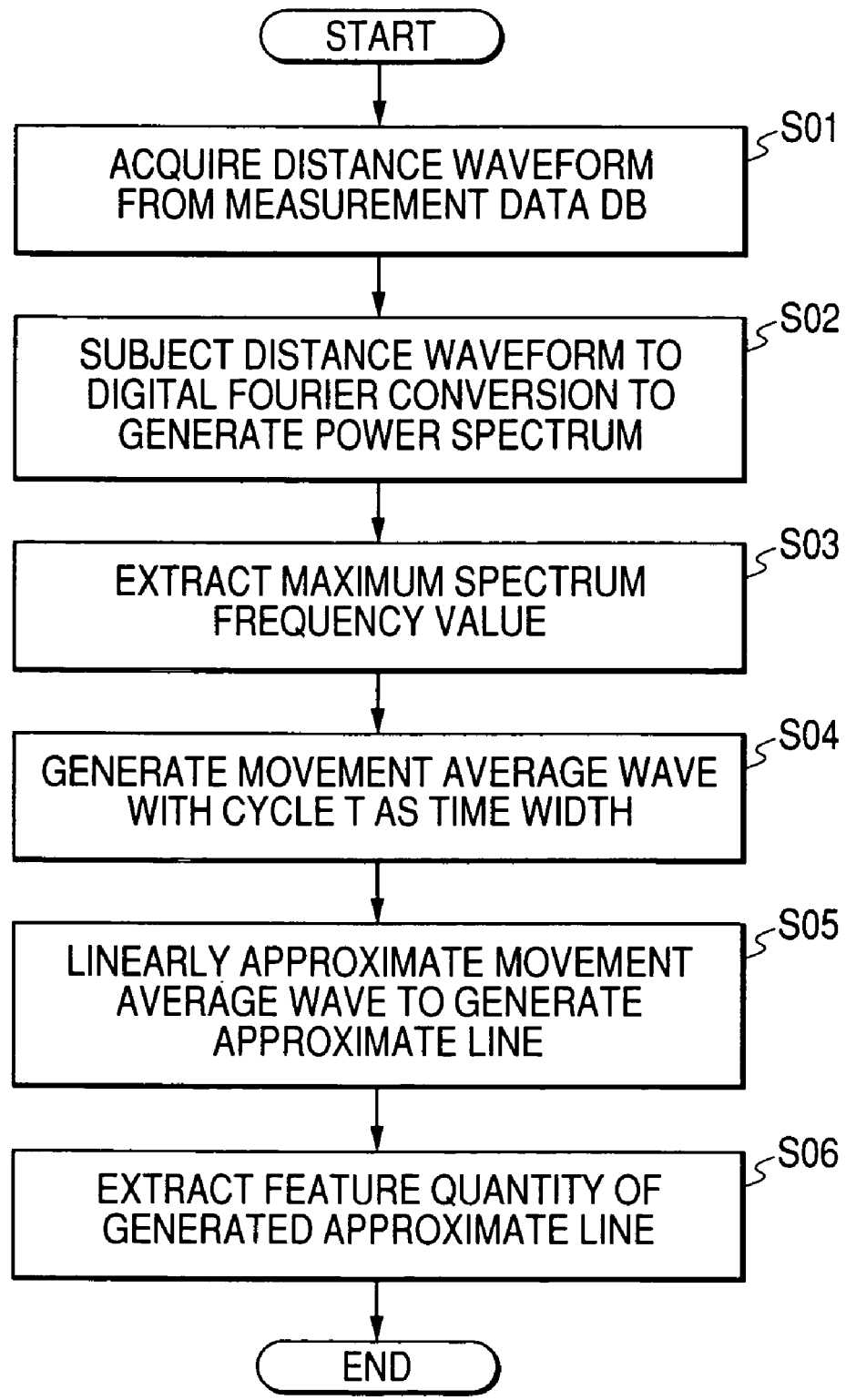
FIG. 14 is a flowchart for explaining an envelope curve generating process of the movement analysis display apparatus in the case of generating an envelope curve in the distance waveform.

FIG. 14 is a flowchart for explaining an envelope curve generating process of the movement analysis display apparatus in the case of generating the envelope curve in the distance waveform.

The distance waveform has already been recorded in the measurement data DB 212 of the movement analysis display apparatus in the above-mentioned procedure.

First, the envelope curve generating means 214 acquires the distance waveform from the measurement data DB 212 (Step S01).

Subsequently, the envelope curve generating means 214 subjects the distance waveform to digital Fourier transformation by the frequency analyzing means 214*a* to generate a power spectrum (Step S02).

Then, the envelope curve generating means 214 extracts the maximum spectrum frequency value by the frequency analyzing means 214*a* to calculate an inverse thereof as the cycle T (Step S03).

Then, the envelope curve generating means 214 generates the cycle T as the time width in the distance waveform by the movement averaging means 214*b* (Step S04).

Then, the envelope curve generating means 214 linearly approximates the movement average wave by the linearly approximating means 214*c* to generate the approximate line (Step S05).

Then, the envelope curve generating means 214 extracts the feature quantity of the generated approximate line by the linearly approximating means 214*c* (Step S06).

Third Embodiment

Subsequently, a description will be given of a movement analysis display apparatus according to a third embodiment with reference to the drawings.

In the third embodiment, a movement is analyzed on the basis of movement information that has been integrated with respect to time.

The third embodiment has the characteristic structure in the analysis processing section 21 within the information processing section 2 as compared with the first embodiment. Accordingly, in the description of the third embodiment, particularly, the analysis processing section 21 will be described in detail, but the duplicated description of the first embodiment will be omitted.

(Analysis Processing Section)

Figure 15:
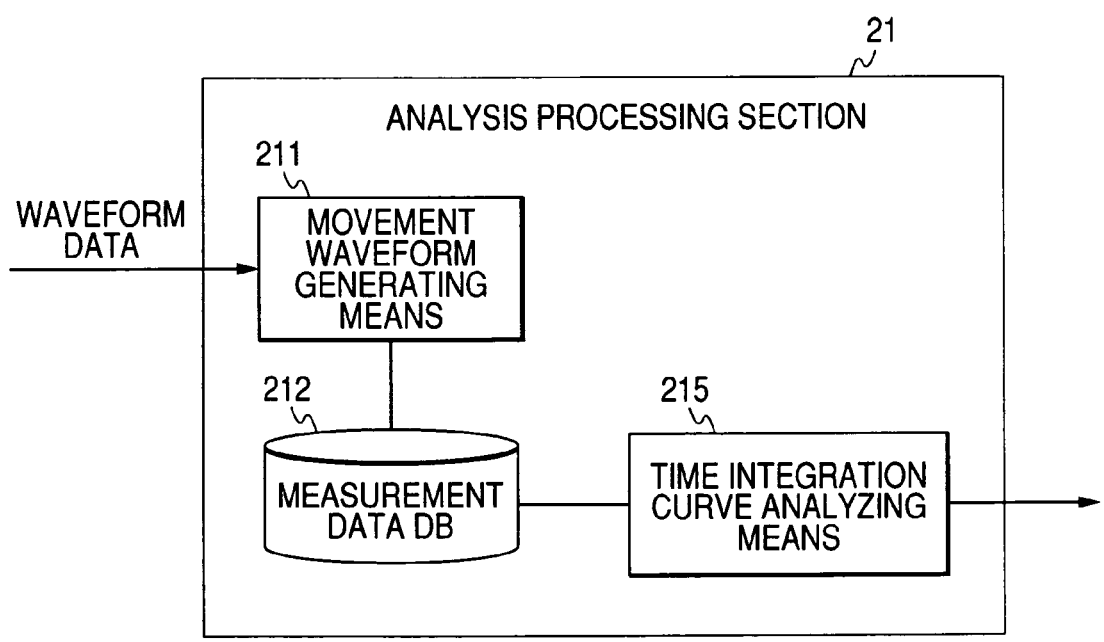
FIG. 15 is a block diagram showing the structure of an analysis processing section according to a third embodiment.

FIG. 15 is a block diagram showing the structure of the analysis processing section 21 according to the third embodiment.

In this example, the analysis processing section 21 according to the third embodiment includes movement waveform generating means 211, measurement data DB 212, and time integration curve analyzing means 215.

[Time Integration Curve Analyzing Means]

Figure 16:
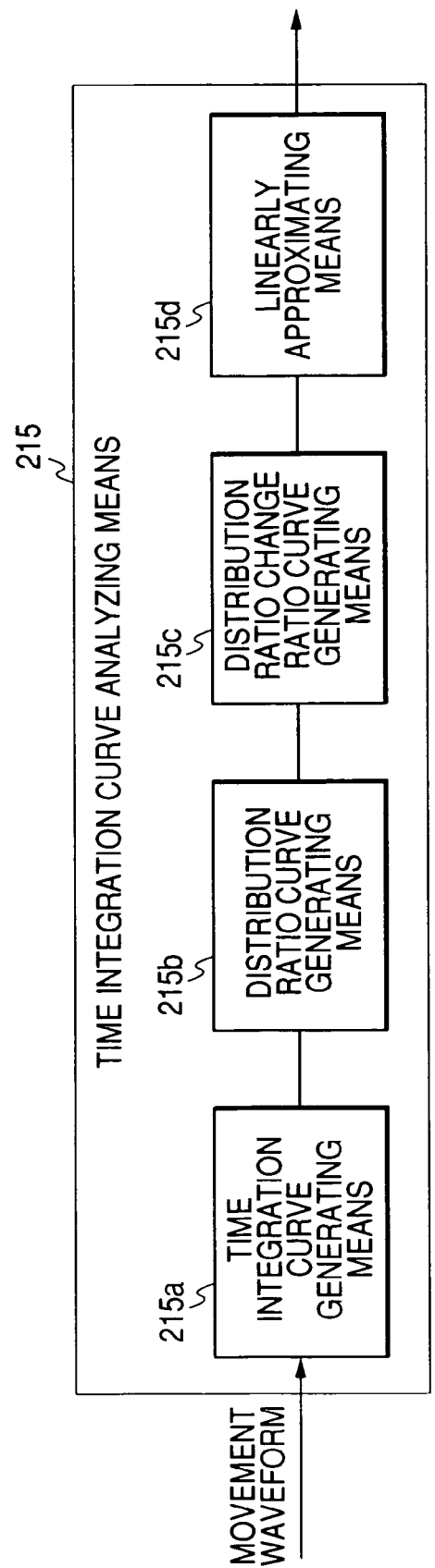
FIG. 16 is a block diagram showing the structure of time integration curve analyzing means according to the third embodiment.

FIG. 16 is a block diagram showing the structure of the time integration curve analyzing means 215. As shown in FIG. 16, the time integration curve analyzing means 215 generates the time integration curve of the movement waveform, and analyzes the time integration curve, to thereby obtain the tendency of the respective movement waveforms.

In this example, the time integration curve analyzing means 215 includes time integration curve generating means 215*a*, distribution ratio generating means 215*b*, distribution ration change rate curve generating means 215*c*, and linearly approximating means 215*d*.

<Time Integration Curve Generating Means>

The time integration curve generating means 215*a* add absolute values in the respective movement waveforms together every time a time elapses to generate the integration curve.

Figure 17A:
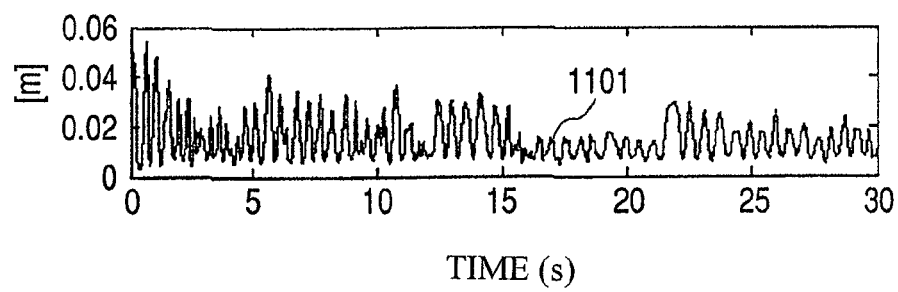
FIGS. 17A to 17C are graphs showing processes during which the distance waveform is integrated with respect to time, respectively.
Figure 17B:
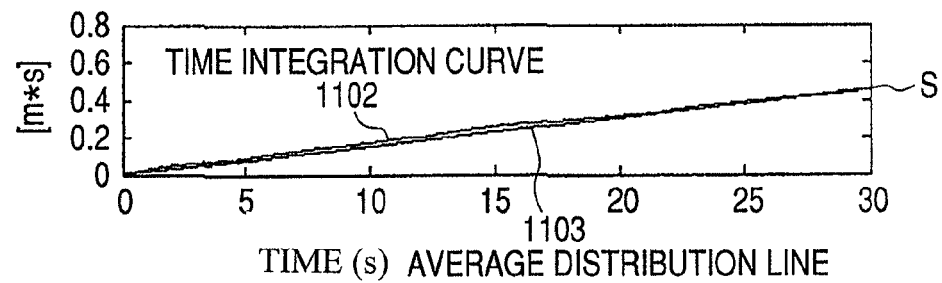
Figure 17C:
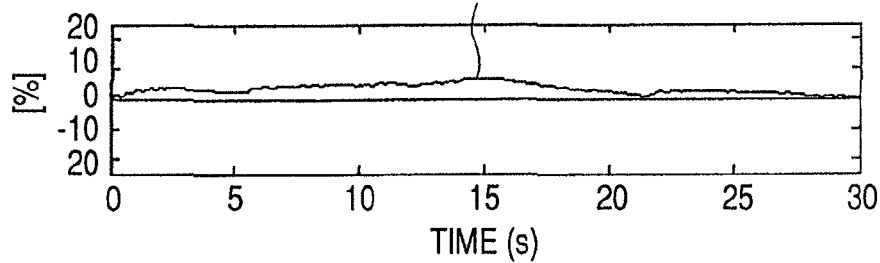

FIGS. 17A to 17C are diagrams showing a process during which the distance waveform is integrated with time, in which FIG. 17A shows a distance waveform, FIG. 17B is a time integration curve, and FIG. 17C is a distribution ratio curve.

The time integration curve generating means 215*a* is capable of obtaining a time integration curve 1102 from the distance waveform (corresponding to a time waveform in Expression (8) that will be described later) 1101 by using the following expression (8).

$$\text{Time integration curve } (n) = [\Sigma \text{ time waveform } (m)] / \text{sampling frequency} \qquad (8)$$

where m=1 to n.

In the example, in FIG. 17B, an integration value at an end point is called "time integration curve (End)", and can be dealt with as the feature quantity of the movement waveform.

In this example, the time integration curve 1102 that has been generated by the time integration curve generating means 215*a* is outputted to the distribution ratio curve generating means 215*b*.

<Distribution Ratio Curve Generating Means>

The distribution ratio curve generating means 215*b* extracts the feature quantity in the time integration curve 1102.

Now, referring to FIGS. 17B and 17C, a description will be given of a procedure of obtaining the distribution ratio. curve 1104 by the distribution ratio curve generating means 215*b*.

As shown in FIG. 17B, the distribution ratio curve generating means 215*b* draws a line that connects a start point with the end point S of the time integration curve 1102 to generate an average distribution line 1103.

As shown in FIG. 17C, the distribution ratio curve generating means 215*b* then generates the distribution ratio curve 1104 from the time integration curve 1102 and the average distribution line 1103.

In this example, the distribution ratio curve generating means 215b is capable of obtaining the distribution ratio curve 1104 by using the following expression (9).

Distribution ratio curve (n)=[time integration curve (n)−average distribution line (n)]/time integration curve (End)×100%   (9)

In the expression (9), the distribution ratio curve is displayed in percentage by using the time integration curve (End). However, division is not conducted by the time integration curve (End), and a calculation expression of [distribution ratio curve (n)=time integration curve (n)−average distribution line (n)] may be applied instead of the expression (9).

As described above, the distribution ratio curve 1104 is generated, thereby making it possible to evaluate the distribution ratio (how dispersion is made from the average distribution line) of the time integration curve 1102.

In this example, the distribution ratio curve 1104 that has been generated by the distribution ratio curve generating means 215b is outputted to the distribution ratio change rate curve generating means 215c.

In the above description, the distance waveform is processed by the time integration curve generating means 215a, but other movement waveforms can be also processed as with the distance waveform.

Figure 18A:
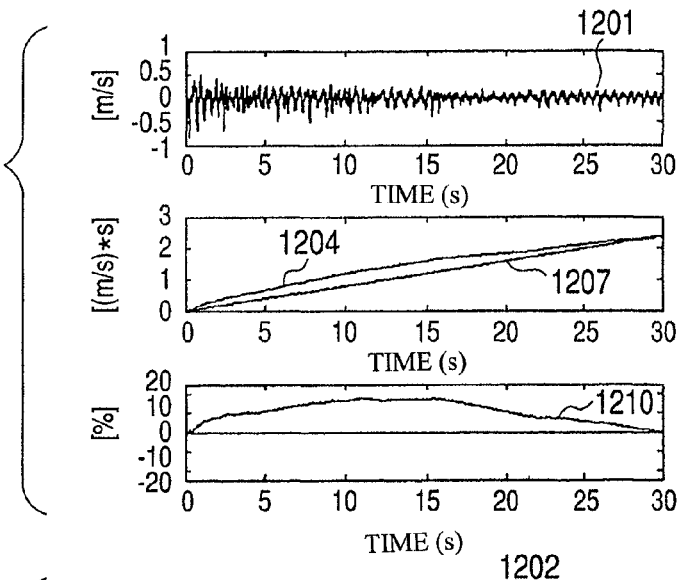
FIGS. 18A to 18C are graphs showing other distance waveforms that are integrated with respect to time.
Figure 18B:
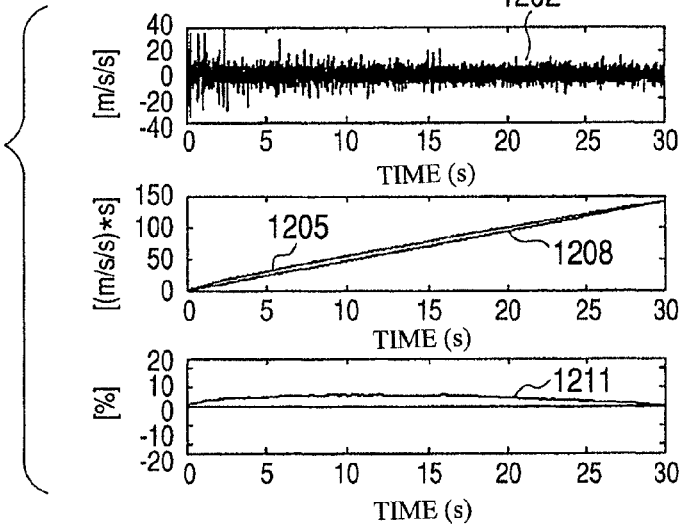
Figure 18C:
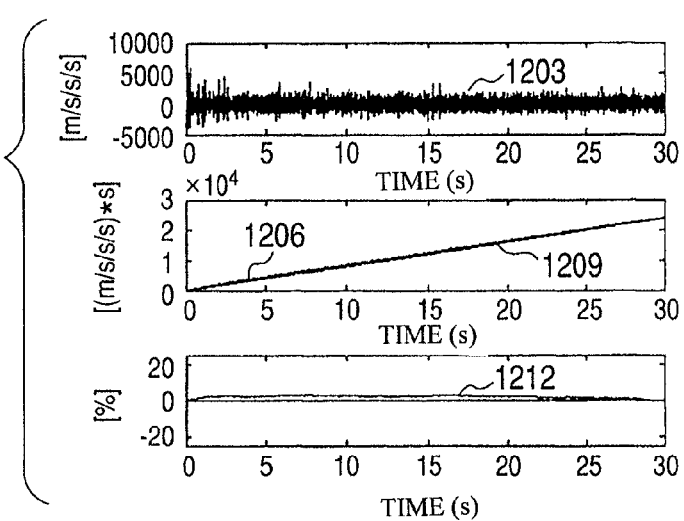

FIGS. 18A to 18C are diagrams showing a velocity waveform, an acceleration waveform, and a jerk waveform which have been processed by the time integration curve generating means 215a, respectively. In this example, a curve indicated by reference numeral 1201 is the velocity waveform, a line indicated by reference numeral 1204 is the time integration curve of the velocity waveform, a line indicated by reference numeral 1207 is the average distribution line related to the velocity waveform, and a curve indicated by reference numeral 1210 is the distribution ratio curve related to the velocity waveform. Also, a curve indicated by reference numeral 1202 is the acceleration waveform, a curve indicated by reference numeral 1205 is the time integration curve of the acceleration waveform, a line indicated by reference numeral 1208 is the average distribution line related to the acceleration waveform, and a curve indicated by reference numeral 1211 is the distribution ratio curve related to the acceleration waveform. Also, a curve indicated by reference numeral 1203 is a jerk waveform, a curve indicated by reference numeral 1206 is a time integration curve of the jerk waveform, a line indicated by reference numeral 1209 is an average distribution line related to the jerk waveform, and a curve indicated by reference numeral 1212 is a distribution ratio curve related to the jerk waveform.

<Distribution Ratio Change Rate Curve Generating Means>

The distribution ratio change rate curve generating means 215c first smoothes the distribution ratio curve 1104, and thereafter differentiates the smoothed curve with respect to time to obtain the distribution ratio change rate curve.

In this example, a description will be given of a procedure of obtaining the distribution ratio change rate curve by the distribution ratio change rate curve generating means 215C with reference to FIGS. 19 and 21A.

Figure 19:
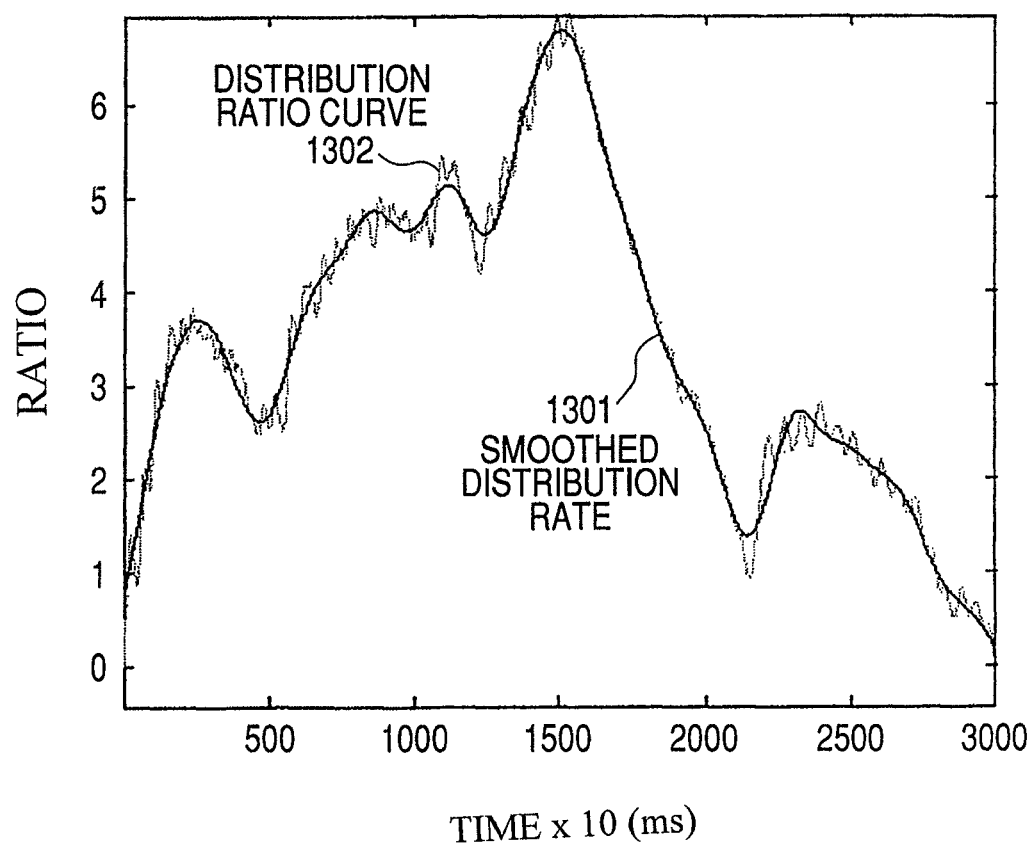
FIG. 19 is a graph showing a distribution ratio of a smoothed distance.

FIG. 19 is a graph showing the smoothed distribution ratio curve. Also, FIGS. 21A to 21D are diagrams showing distribution ratio change curves obtained by differentiating the smoothed distribution ratio curve with respect to time, in which FIG. 21A is a distribution ratio change curve that is derived from the time integration curve of the distance waveform. Likewise, FIG. 21B is a distribution ratio change curve that is derived from the velocity waveform, FIG. 21C is a distribution ratio change curve that is derived from the acceleration waveform, and FIG. 21D is a distribution ratio change curve that is derived from the jerk waveform, respectively.

First, the distribution ratio change rate curve generating means 215c smoothes the distribution ratio curve 1302 into the distribution ratio curve 1301 as shown in FIG. 19. In this case, the distribution ratio curve 1302 is smoothed by removing a high frequency component, for example, discrete wavelet analysis. In addition, as the wavelet function, it is preferable that Daubechies 10 are used as the distribution ratio curve 1301 from which components including level 7 or lower levels are removed to smooth the remaining components. A method of smoothing the distribution ratio curve 1302 is not limited to the discrete wavelet analysis, and for example, the distribution ratio curve 1302 may be smoothed by conducting a low-pass filter (LPF) process.

Subsequently, the distribution ratio change rate curve generating means 215c differentiates a smoothed distribution ratio curve 1301 with respect to time, to thereby obtain a distribution ratio change rate curve 1501 as shown in FIG. 21A.

The distribution ratio change rate curve generating means 215c is capable of obtaining the distribution ratio change rate curve 1501 by using the following expression (10).

Distribution ratio change rate curve (n)=[distribution ratio curve (n+1)−distribution ratio curve (n)]× sampling frequency   (10)

According to the distribution ratio change rate curve 1501 thus obtained, any point at which the smoothness of movement of the fingers is short can be visually and quantitatively understood.

In the above description, the distance waveform is processed by the distribution ratio change rate curve generating means 215c. Likewise as the distance waveform, other movement waveforms can also be processed.

Figure 20A:
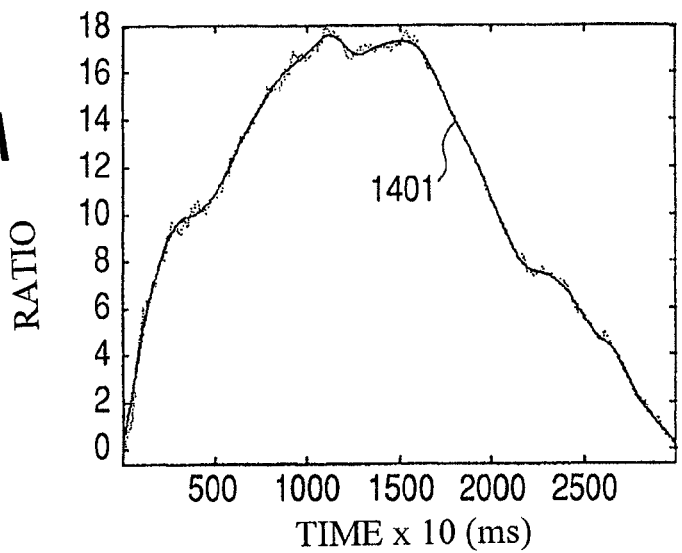
FIGS. 20A to 20C are graphs showing other smoothed distribution ratio curves, respectively.
Figure 20B:
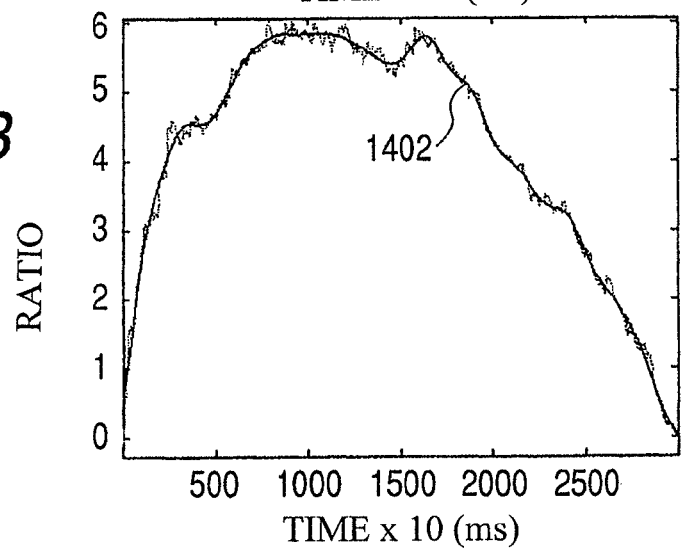
Figure 20C:
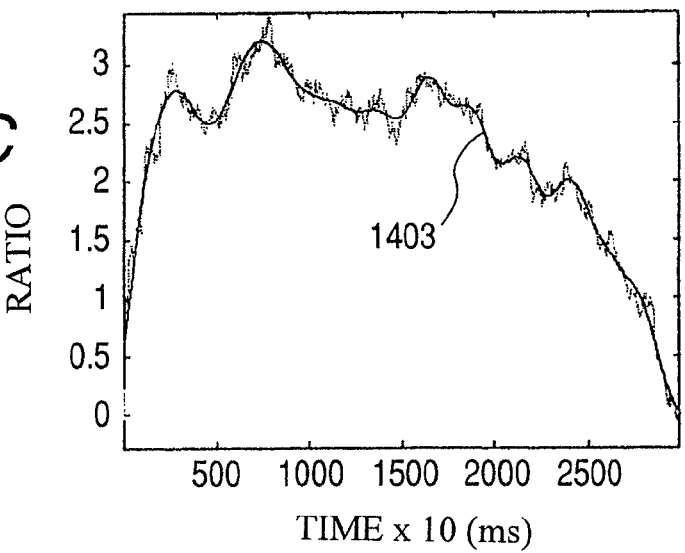

FIGS. 20A to 20C are diagrams showing the smoothed distribution ratio change curve related to the velocity waveform, the acceleration waveform, and the jerk waveform, respectively. In this example, a curve indicated by reference numeral 1401 is a smoothed distribution ratio curve related to the velocity waveform. Also, a curve indicated by reference numeral 1402 is a smoothed distribution ratio curve related to the acceleration waveform. Further, a curve indicated by reference numeral 1403 is a smoothed distribution ratio curve related to the jerk waveform.

As described above, FIGS. 21B to 21D are distribution ratio change rate curve related to the velocity waveform, the acceleration waveform, and the jerk waveform. In this example, a curve indicated by reference numeral 1502.is a distribution ratio change rate curve related to the velocity waveform. Also, a curve indicated by reference numeral 1503 is a distribution ratio change rate curve related to the acceleration waveform. Further, a curve indicated by reference numeral 1504 is a distribution ratio curve rate curve related to the acceleration waveform.

<Linearly Approximating Means>

The linearly approximating means 215d linearly approximates the distribution ratio change rate curve to generate the approximate line.

In this example, FIG. 22 is a graph showing an approximate line obtained by linearly approximating the distribution ratio change rate curve to generate the approximate line.

As shown in FIG. 22, the linearly approximating means linearly approximates the distribution ratio change rate curve 1602 to generate the approximate line 1601.

Subsequently, the linearly approximating means 215d extracts the feature quantity of the generated approximate line 1601. The feature quantity of the extracted approximate line 1601 is, for example, a slope, a section, or a dispersion value from the approximate line.

As described above, the distance waveform is processed by the linearly approximating means. Likewise as the distance waveform, other movement waveforms can be also processed.

Figure 23A:
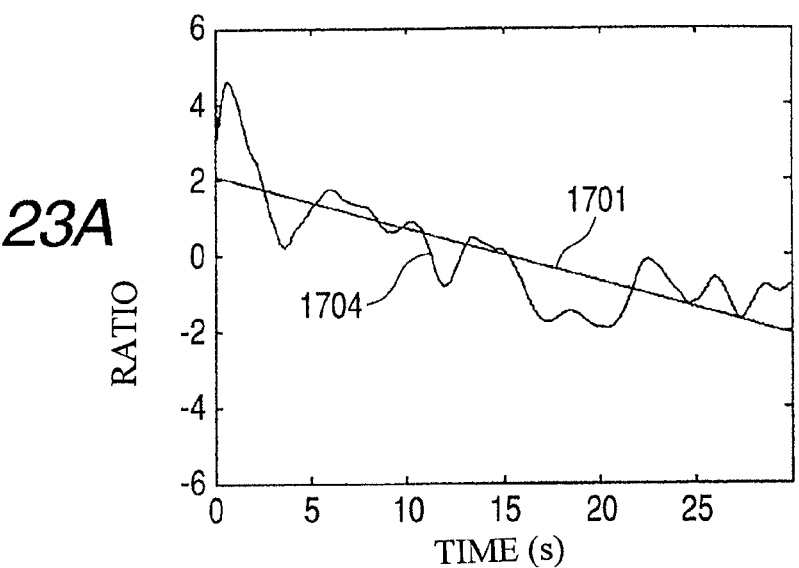
FIGS. 23A to 23C are graphs showing approximate lines into which distribution ratio change rate curves based on other movement waveforms are linearly approximated, respectively.
Figure 23B:
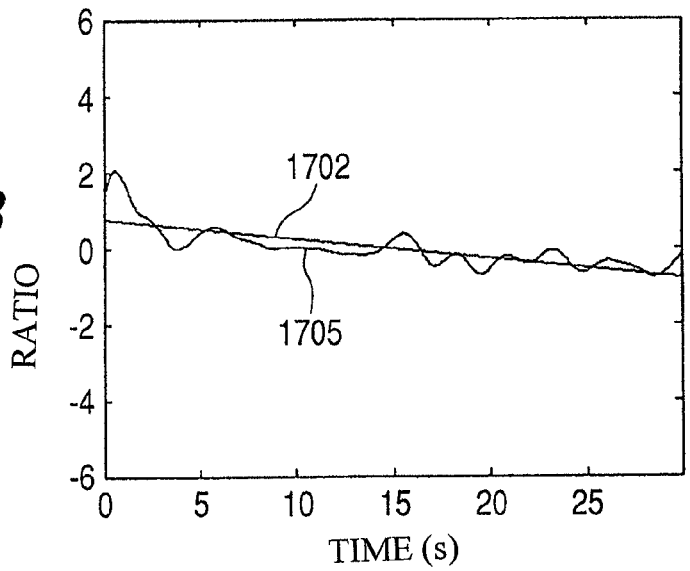
Figure 23C:
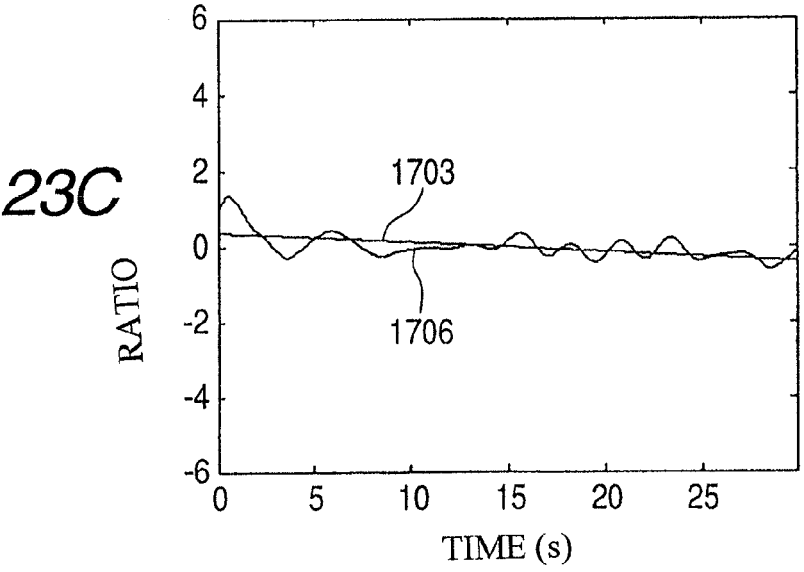

FIGS. 23A to 23C are diagrams showing the distribution ratio curve related to the velocity waveform, the acceleration waveform, and the jerk waveform which have been processed by the linearly approximating means, respectively. In this example, a curve indicated by reference numeral 1701 is an approximating line related to the velocity waveform, and a curve indicated by a reference numeral 1704 is a distribution ratio change rate curve related to the velocity waveform. Also, a curve indicated by reference numeral 1702 is an approximate line related to the acceleration waveform, and a curve indicated by reference numeral 1705 is a distribution ratio change rate curve related to the acceleration waveform. Also, a curve indicated by reference numeral 1703 is an approximate line related to the jerk waveform, and a curve indicated by reference numeral 1706 is a distribution ratio change rate curve related to the jerk waveform.

In this example, this embodiment is described with reference to the drawing showing data that assumes the Parkinson's patient. However, in the case where the movement analysis display apparatus 1 of this embodiment is applied to the healthy subject, a tendency is made that the gentle distribution ratio curve or distribution ratio change rate curve is displayed on the display means 4, for example, as compared with the Parkinson's patient. Also, for example, a tendency is made to display a time integration curve (End) having a value that is relatively larger than that of the Parkinson's patient.

As described above, the time integration curve analyzing means 215 generates the time integration curve and extracts the feature of the time integration curve, thereby making it possible to evaluate whether the movement of the subject is uniformly conducted or not, or evaluate the arrival energy that has been achieved by the subject.

<<Others>>

As described above, this embodiment is capable of obtaining the following advantages.

The movement waveform such as the distance waveform, the velocity waveform, the acceleration waveform, or the jerk waveform can be generated and analyzed on the basis of the waveform data that has been detected by the movement sensor. Thus, the plural movement waveforms are generated to analyze the movement of the subject, thereby making it possible to conduct the evaluations from various angles. In particular, the jerk waveform is generated, thereby making it possible to evaluate the awkwardness of the subject.

Also, according to the first embodiment, the energy balance value of the movements in the positive direction and the negative direction can be calculated and analyzed on the basis of the velocity waveform. Thus, the energy balance value is calculated, thereby making it easy to compare different subjects with each other on the basis of the negative second-power integration value that is small in the individual difference.

Also, according to the second embodiment, the envelope curve can be generated and analyzed on the basis of the distance waveform. Thus, the envelope curve is generated in the distance waveform, thereby making it possible to evaluate the entire tendency of the distance waveform.

Also, according to the third embodiment, the time integration curve can be generated and analyzed in the respective movement waveforms. Thus, the time integration curve is generated, thereby making it possible to evaluate whether the movement of the subject is uniformly conducted or not, and evaluate the arrival energy that has been achieved by the subject.

This embodiment is not limited by the above embodiments, and various variations can be conducted within the limit of its technical concept.

For example, the analysis result that has been outputted by the analysis processing section may be not only outputted as it is, but also outputted after being subjected to statistical processing. In this case, a statistical processing section is disposed within the information processing section, and the analysis result is grouped (for example, sectioned into a healthy subject group and individual disease groups) on the basis of the subject information that has been recorded in the subject DB not shown, thereby making it possible to execute the statistic processing (for example, the calculation of an average value or a dispersion value).

Also, in this embodiment, the movement average wave is generated to produce the envelope curve. However, a method of generating the envelope curve is not limited to the above-mentioned method. For example, the maximum values at a given time width of the distance waveform are coupled to produce the envelope curve. Alternatively, the minimum values at a given time width of the distance waveform are coupled to produce the envelope curve.

A movement analyzing method using a movement analysis display apparatus having analyzing means for analyzing waveform data of a time series that is acquired from a movement sensor, and display means for displaying an analysis result that is analyzed by the analyzing means, the movement analysis method includes the steps of: generating a movement waveform corresponding to the waveform data from the waveform data to generate a distance waveform from the movement waveform; and generating an envelope curve at a given time width in the distance waveform.

The movement analyzing method using a movement analysis display apparatus further includes the step of linearly approximating the envelope curve to generate an approximate line after the envelope curve generating step.

In the movement analyzing method using a movement analysis display apparatus, the envelope curve generating step includes the steps of: conducting a frequency analyzing operation of the distance waveform to obtain the maximum spectrum frequency; and generating a movement average wave with a time width having an inverse of the maximum spectrum frequency as a cycle in the distance waveform.

The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A movement function analysis display apparatus, comprising:
   a movement sensor for sensing and acquiring movement data of a live subject including waveform data of a time series;
   an analyzing unit coupled to the movement sensor, for analyzing the waveform data of the time series which is acquired from the movement sensor; and
   a display unit for displaying an analysis result that is analyzed by the analyzing unit,
   wherein the analyzing unit comprises:
   a movement waveform generating unit for generating a movement waveform corresponding to the waveform data from the waveform data, and for generating a velocity waveform from the movement waveform; and
   an energy balance value calculating unit for evaluating a movement energy ratio in positive and negative directions by using a positive velocity value and a negative velocity value from the velocity waveform,
   wherein the energy balance value calculating unit calculates a second-power integration value of the positive velocity value and a second-power integration value of the negative velocity value in the velocity waveform,
   wherein the energy balance value calculating unit calculates an energy balance value from a ratio of the second-power integration values after the second-power integration values are calculated, and
   wherein the analyzing unit evaluates the movement energy ratio in the positive and negative directions from the energy balance value, and determines a severity of a functional disorder of the live subject based on a magnitude of the movement energy ratio in the positive and negative directions so as to produce the analysis result for a visual display on the display unit.

2. The movement function analysis apparatus according to claim 1, wherein the live subject is a Parkinson's patient.

3. The movement function analysis apparatus according to claim 1, wherein the functional disorder of the live subject is a brain disorder which includes a Parkinson's disease.

* * * * *